US010456099B2

(12) United States Patent
Onouchi

(10) Patent No.: US 10,456,099 B2
(45) Date of Patent: Oct. 29, 2019

(54) RADIATION DETECTING DEVICE AND MEDICAL IMAGING DEVICE

(71) Applicant: HITACHI, LTD., Tokyo (JP)

(72) Inventor: Masafumi Onouchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 166 days.

(21) Appl. No.: 15/746,482

(22) PCT Filed: Aug. 1, 2016

(86) PCT No.: PCT/JP2016/072479
§ 371 (c)(1),
(2) Date: Jan. 22, 2018

(87) PCT Pub. No.: WO2017/033675
PCT Pub. Date: Mar. 2, 2017

(65) Prior Publication Data
US 2018/0206805 A1    Jul. 26, 2018

(30) Foreign Application Priority Data

Aug. 24, 2015   (JP) .................................. 2015-165173

(51) Int. Cl.
*A61B 6/00*         (2006.01)
*A61B 6/03*         (2006.01)
(Continued)

(52) U.S. Cl.
CPC ............ *A61B 6/4241* (2013.01); *A61B 6/032* (2013.01); *A61B 6/40* (2013.01); *A61B 6/4233* (2013.01);
(Continued)

(58) Field of Classification Search
CPC ... A61B 6/4233; A61B 6/4241; A61B 6/4266; A61B 6/4275
See application file for complete search history.

(56) References Cited

U.S. PATENT DOCUMENTS

2003/0185342 A1* 10/2003 Petrick ................... H04N 5/235
                                                          378/98.8
2008/0099689 A1*  5/2008 Nygard ................. G01T 1/2018
                                                          250/370.09
2013/0010921 A1   1/2013 Sagoh et al.

FOREIGN PATENT DOCUMENTS

JP       2000-131440       5/2000
JP       2013-227          1/2013

OTHER PUBLICATIONS

International Search Report dated Oct. 25, 2016 in connection with PCT/JP2016/072479.

* cited by examiner

*Primary Examiner* — David P Porta
*Assistant Examiner* — Mamadou Faye
(74) *Attorney, Agent, or Firm* — Cooper & Dunham LLP

(57) ABSTRACT

There is provided a configuration that allows implementation of both photon measurement and current measurement with practical measuring performance and circuit area, where a plurality of detector elements constituting one detector pixel are connected to photon measuring circuits on a one-to-one basis, thereby counting current pulse signals outputted from the detector elements, and a current measuring unit incorporates an integrator, an adder, and a sample-hold circuit provided for every detector pixel, and a converter for converting analogue signals to digital signals, one converter being provided for a plurality of detector pixels. The integrator integrates and the adder adds current pulse signals respectively outputted from the plurality of detector elements constituting one detector pixel, the sample-hold circuit integrates outputs from the adder, and the converter selectively converts analogue outputs from the integration circuit of any of the plurality of detector pixels.

20 Claims, 14 Drawing Sheets

(51) Int. Cl.
*G01N 23/046* (2018.01)
*G01T 1/24* (2006.01)
*G06T 11/00* (2006.01)

(52) U.S. Cl.
CPC ................ *A61B 6/463* (2013.01); *A61B 6/54* (2013.01); *G01N 23/046* (2013.01); *G01T 1/247* (2013.01); *G06T 11/003* (2013.01)

FIG. 1
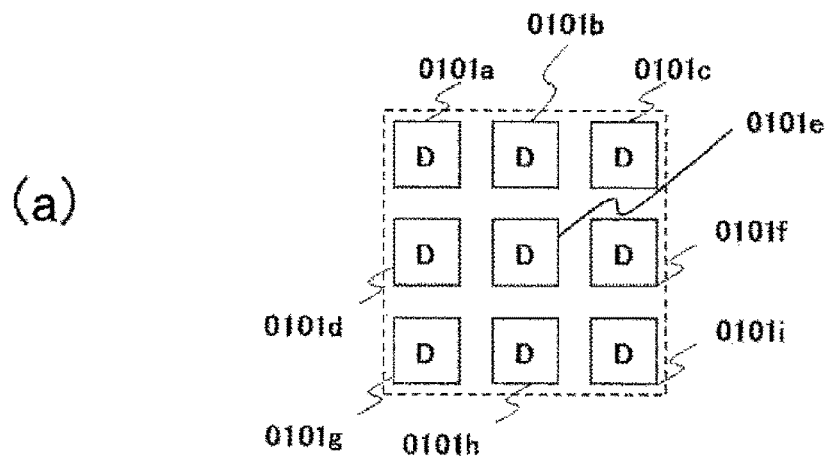
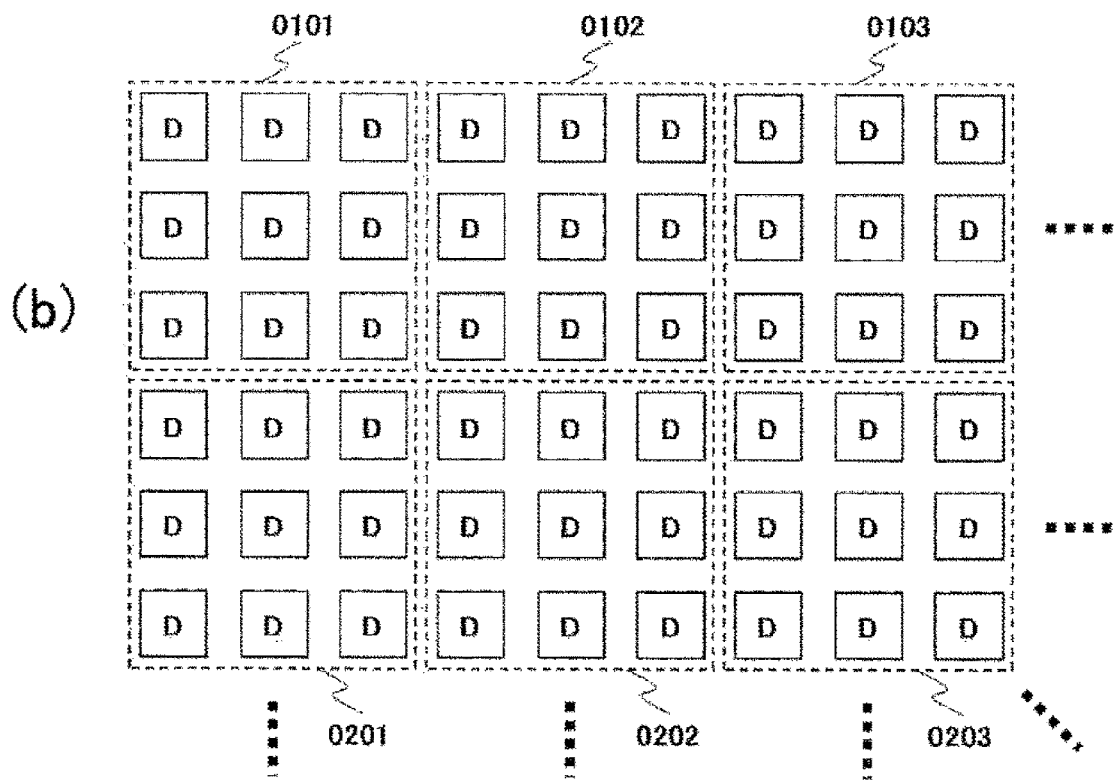

RADIATION DETECTING DEVICE AND MEDICAL IMAGING DEVICE

TECHNICAL FIELD

The present invention relates to a radiation detection device including a radiation detector that comprises a plurality of semiconductor cells configured to acquire photon measurement data and current measurement data simultaneously, and a medical imaging system.

BACKGROUND ART

In recent years, development of photon counting CT (Computed Tomography) devices has been carried forward, equipped with a detector that employs a photon counting mode (a photon counting detector). Unlike a detector of charge integration type, which is employed in conventional CT devices, the photon counting detector is capable of counting x-ray photons individually, which have been entered into detector elements. This configuration allows measurement of energy of the entered x-ray photons on a photon-by-photon basis, featuring that much more information can be obtained when compared to the conventional CT devices.

The detector element in the photon counting detector is provided with a semiconductor layer made of cadmium zinc telluride (CZT), cadmium telluride (CdTe), or the like, and outputs a pulse signal every time the x-ray photon is entered, in response to thus entered x-ray photon.

However, time is required for the detector element to generate the pulse signal and for a measuring circuit to repose, which measures the pulse signal outputted from the detector element. Therefore, it is known that if X-rays are incident at a high rate, a subsequent x-ray photon is prone to be entered, prior to attenuation of the pulse signal of the x-ray photon previously entered, resulting in that the pulse signals are piled up. This phenomenon is referred to as "pile-up", and due to this phenomenon, the photon counting detector may fail to measure correctly the number of x-ray photons and its energy. To address this problem, there is known a photon counting detector comprising a plurality of detector elements arranged in a region corresponding to one pixel, where X-rays are divided in a planar fashion and detected respectively, thereby adjusting the amount of the x-ray photons entered into one detector element, and reducing such generation of pile-up.

In a conventional CT device, a charge integration detector is employed, and a method has fairly matured, where an image is generated from measured data (current data) acquired by this charge integration detector, and a diagnosis is performed by using thus generated image. Therefore, it is also desired in a photon counting CT device, to acquire data of current simultaneously, in addition to an output of counting x-ray photons. In order to achieve this object, there is disclosed in the patent document 1, a circuit configuration where detector elements using CdTe are connected to both a photon measuring circuit and a current measuring circuit.

PRIOR ART DOCUMENT

Patent Document

Patent Document 1: Japanese Unexamined Patent Application Publication No. 2000-131440

DISCLOSURE OF THE INVENTION

Problems to be Solved by the Invention

In an actual system, when both the x-ray photon measurement and the integrated current measurement are performed simultaneously, it is desirable to bring the area of the measuring circuits into the same level of area of a group of detector elements, while achieving practical measuring performance in both measurements. By limiting the area of the measuring circuits to the same level of area of the group of detector elements, it is possible to arrange a substrate on which the detector elements are mounted and a substrate (LSI) of the measuring circuits, in a manner superimposed one on another. Therefore, this may prevent the system from being oversized, allowing manufacturing costs to be held down.

As target performance for withstanding practical use in a CT system, for instance, when the size of a pixel is 1 $mm^2$, it is desirable that the overall area of the measuring circuits should be 1 $mm^2$/pixel or less, photon measuring performance should be 450 M photons/$mm^2$/sec or mere, and current measuring performance should have a measuring velocity of 3 k sample/sec or higher with 20-bit measurement precision. However, it is difficult for conventional techniques to achieve all of such performance as described above concurrently. This situation will be described in the following.

Firstly as preconditions, the photon measuring circuit in an optimized design, presently used, has the circuit area of 0.09 $mm^2$/pixel, and counting performance is around 50M photons/$mm^2$/sec. On the other hand, the current measuring circuit has the circuit area of around 6 $mm^2$, with 20-bit measurement precision and the measuring velocity of around 200 k sample/sec. The current measuring circuit requires a high degree of measuring precision, and its area is prone to be large. Therefore, conventionally, one current measuring circuit is provided for a plurality of pixels, and it is time-shared by those pixels, in general. By way of example, if the current measuring circuit is time-shared by every 64 pixels, the area per pixel is 0.094 $mm^2$, and the measuring velocity is 3.1 k sample/sec (hypothetical conditions).

Under those hypothetical conditions, as disclosed in the Patent Document 1, assuming that one photon measuring circuit (high-speed waveform shaping circuit 5a, a flip flop 7a, an encoder 8, and the like) is arranged for one pixel (such as a semiconductor cell 1a), together with placing the current measuring circuit (a multiplexer 72 and an A/D converter 73) shared by every 64 pixels, a total circuit area of the photon measuring circuit and the current measuring circuit for each pixel of 1 $mm^2$, becomes 0.18 $mm^2$/pixel, the photon measuring performance 450M photons/$mm^2$/sec, and the current measuring performance has the measuring velocity of 3.1 k sample/sec with 20-bit precision. Therefore, the targeted photon measuring performance of 450M photons/$mm^2$/sec cannot be attained. As described so far, it is difficult for conventional techniques to achieve a configuration where the circuit area, the photon measuring performance, and the current measuring performance concurrently satisfy the target performance.

An object of the present invention is to provide a configuration that allows implementation both of photon measurement and current measurement, with practical measuring performance and circuit area.

Means for Solving the Problems

A radiation detection device of the present invention comprises a plurality of detector elements for generating current pulse signals upon receipt of photons of radiation, and a photon measuring unit and a current measuring unit being connected to the detector elements. The detector elements are arranged in a specified array, and every predetermined number of detector elements constitutes one detector pixel. The photon measuring unit includes a plurality of photon measuring circuits connected to the detector elements on a one-to-one basis, for counting the current pulse signals outputted from the detector elements.

The current measuring unit comprises an integrator, an adder, and a sample-hold circuit provided for every detector pixel, and a converter for converting an analogue signal to a digital signal, where one converter is provided for the detector pixels more than one. The integrator and the adder perform integration and addition on the current pulse signals outputted respectively from the plurality of detector elements constituting one detector pixel. The sample-hold circuit holds outputs of the addition and integration from the integrator and the adder, with a predetermined timing, and the converter selectively converts analogue outputs from the sample-hold circuit into digital signals, as to any of the plural detector pixels.

Advantage of the Invention

According to the present invention, both the photon measurement and the current measurement can be implemented with practical measuring performance and circuit area.

BRIEF DESCRIPTION OF THE DRAWINGS

FIG. 1(a) illustrates an arrangement of detector elements within a detector pixel according to a first embodiment, and FIG. 1(b) illustrates an array of the detector pixels;

BEST MODE FOR CARRYING OUT THE INVENTION

Embodiments of the present invention will now be described.

First Embodiment

A radiation detection device of a first embodiment will be described with reference to accompanying drawings.

In the radiation detection device of the present embodiment, one detector pixel is divided into plural sub-pixels (detector elements), and a photon measuring circuit is provided for every detector element, thereby enhancing photon measuring performance. In addition, an integrator and an adder are provided for every detector pixel, for adding outputs from the plural detector elements constituting one detector pixel. Then, one A/D converter is provided for a plurality of detector pixels, so as to selectively convert outputs from the adder into digital signals, with regard to the plural detector pixels, whereby current measurement is performed. According to the adder being provided for binding the outputs from the plural detector elements, as to each detector pixel, provision of one A/D converter for plural pixels is sufficient, just like conventionally used methods, and it is possible to prevent increase of circuit area, even with the configuration where the detector pixel is divided into the sub-pixels (detector elements). Descriptions will be provided in the following, with reference to the drawings.

Figure 2:
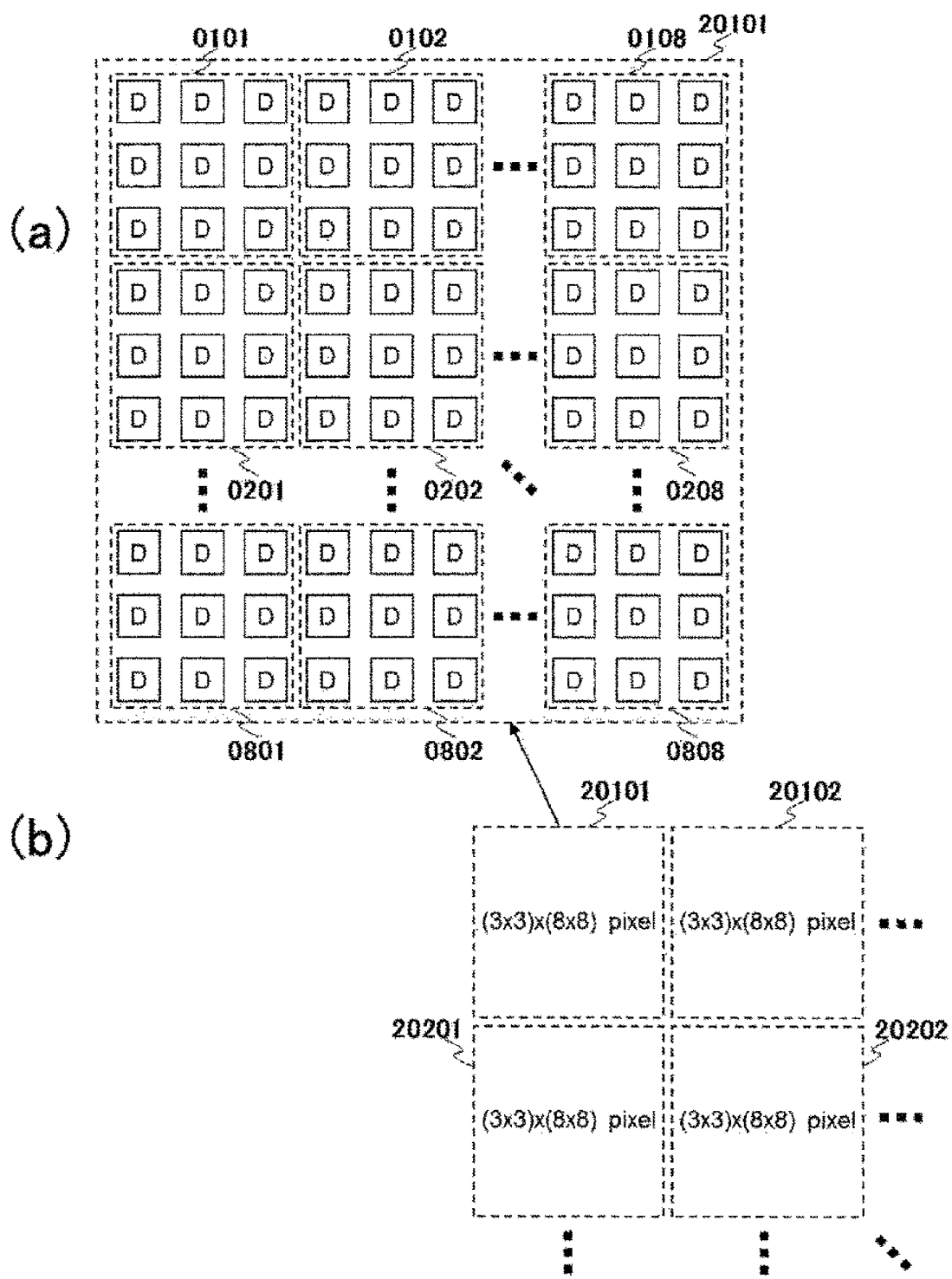
FIG. 2(a) illustrates a process-based relationship between the detector elements and pixels, showing the array of the detector pixels within a detector element substrate according to the first embodiment.
FIG. 2(b) illustrates a state where a plurality of detector element substrates are arranged.

In the present embodiment, as shown in FIG. 1, the detector pixel 0101 for receiving radiation photons and generating current pulse signals, is divided into n (e.g., n=9) sub-pixels (detector elements (D) 0101*a* to 0101*i*). In other words, as shown in FIGS. 1 and 2, plural detector elements (D) are arranged in a specified array, and every predetermined n elements constitute one detector pixel such as 0101. The radiation detection device has a photon measuring unit and a current measuring unit, being connected to the detector elements (D) such as 0101*a* to 0101*i*.

As shown in FIG. 3(a), the photon measuring unit incorporates photon measuring circuits (P) 301*a* to 301*i* connected in a one-to-one basis to the detector elements (D) such as 0101*a* to 0101*i*, and charge amplifiers (A) 313*a* to 313*i* provided respectively between the detector elements (D) such as 0101*a* and the photon measuring circuits (P) such as 301*a*. Each of the detector elements (D) 0101*a* to 0101*i* receives radiation photons, and outputs current pulse signals. The charge amplifiers (A) 313*a* to 313*i* convert the current pulse signals outputted respectively from the detector elements (D) 0101*a* to 0101*i* into voltage pulses.

Figure 3:
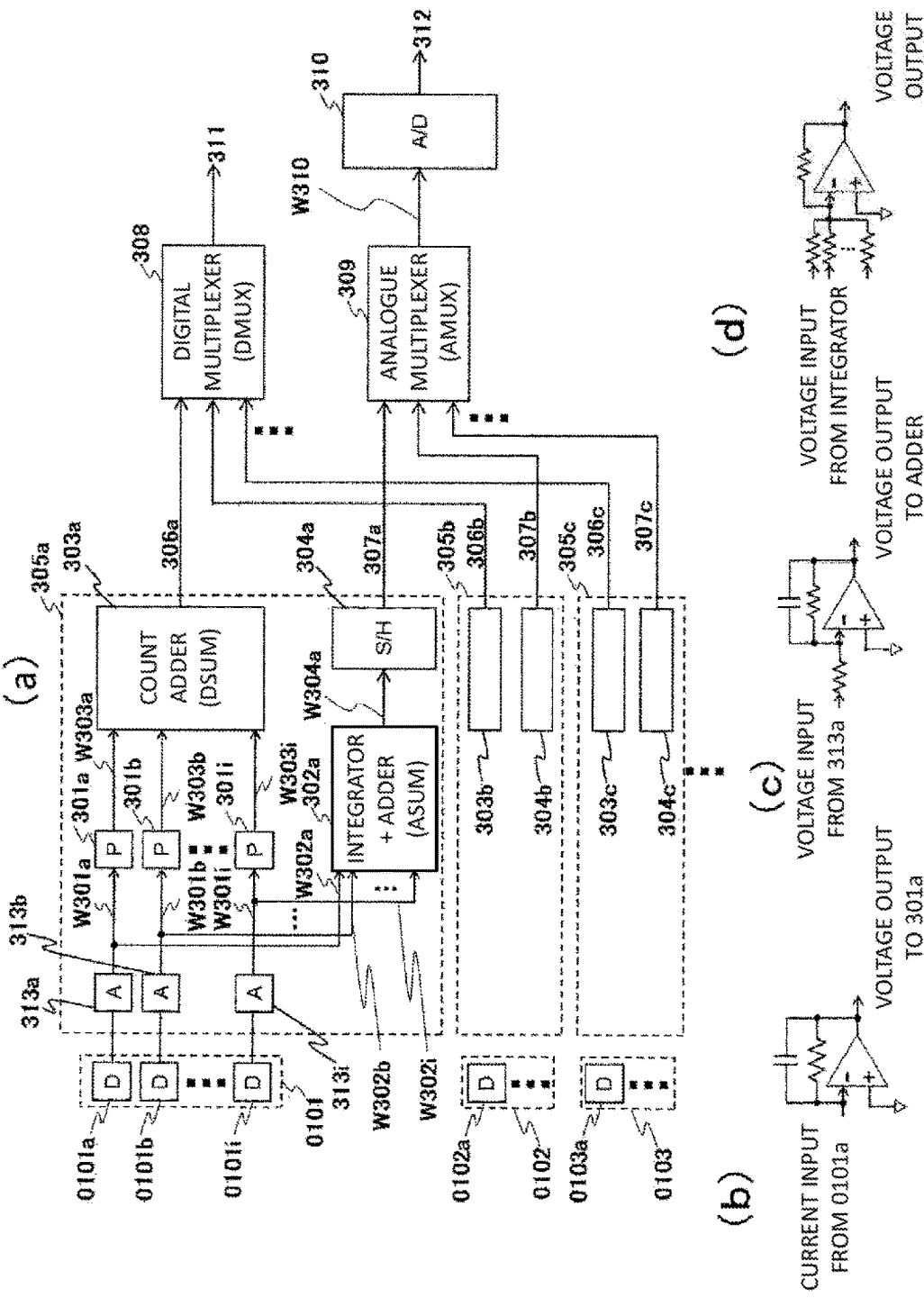
FIG. 3(a) is a block diagram showing a circuit configuration of a radiation detection device according to the first embodiment.
FIG. 3(b) is a circuit diagram showing a configuration example of a charge amplifier.
FIG. 3(c) is a circuit diagram showing a configuration example of an integrator.
FIG. 3(d) is a circuit diagram showing a configuration example of an adder.

The photon measuring circuits (P) 301*a* to 301*i* count, respectively, the voltage pulses outputted from the charge amplifiers (A) 313*a* to 313*i*. With the configuration above, one pixel is divided into sub pixels (detector elements (D) 0101*a* to 0101*i*), then, each sub pixel (detector element (D)) receives radiation photons and outputs current pulses, and the number of the current pulses can be counted after converted into voltage pulses. Therefore, it is possible to prevent a pile-up that occurs when an x-ray photon is detected closely in time with another x-ray photon in the detector element (D). This allows a photon measuring velocity as to one detector pixel 0101 to be n-times higher than the measuring velocity of one photon measuring circuit (P) 301*a*. Accordingly, the photon measurement can be performed at a desired measuring velocity. As the charge amplifiers (A) 313*a* to 313*i*, the circuit as shown in FIG. 3(*b*) may be employed, for instance.

On the other hand, the current measuring unit is provided with the integrator and adder (hereinafter, represented as "integrator+adder") 302*a* and the sample-hold circuit (S/H circuit) 304*a*, which are provided for every detector pixel such as 0101. The integrator+adder 302*a* comprises the integrators, the number of which corresponds to the number of the charge amplifiers (A) 313*a* to 313*i*, and the adder for adding the outputs respectively from those integrators. The circuit as shown in FIG. 3(*c*) may be used as the integrator, for instance, and the circuit as shown in FIG. 3(*d*) may be used as the adder, for instance. An output wire of each of the charge amplifiers (A) 313*a* to 313*i* branches into two, and one (such as W301*a*) is connected to the aforementioned photon measuring circuit (P) such as 301*a*, and the other (such as W302*a*) is connected to the integrator+adder 302*a*.

The integrator+adder 302*a* integrates the voltage pulse signals W301*a* to W301*i*, respectively outputted from the charge amplifiers 313*a* to 313*i*, and further adds the signals. Accordingly, it is possible to obtain a current value, being a total of current pulse signals outputted from n detector elements (D) 0101*a* to 0101*i* in association with one detector pixel 0101. The S/H circuit 304*a* holds outputs from the integrator+adder 302*a* with a predetermined timing.

The current measuring unit further incorporates a converter (A/D converter) 310 that is provided for the plural detector pixels such as 0101, 0102, and 0103, and converts analogue signals into digital signals.

The A/D converter 310 selectively converts analogue outputs to digital signals, the analogue outputs being from the S/H circuits such as 304*a* to 304*c*, as to any of k detector pixels (e.g., 64 pixels) such as 0101 to 0103. Accordingly, the current measuring unit is allowed to perform current measurement on a pixel-by-pixel basis.

In the present embodiment, the integrators+adders such as 302*a* are provided respectively for the detector pixels such as 0101, and current pulse signals outputted from the detector elements (D) are added and combined. Therefore, it is not necessary to directly connect the A/D converter 310 to the sub-pixel (detector element (D)), but only one A/D converter is needed for k detector pixels including 0101. Accordingly, though it is configured such that one pixel is divided into n sub-pixels (detector elements (D)), current measurement can be performed without increasing the number of the A/D converter 310 that has the largest area in the current measuring unit. Therefore, the circuit area of the current measuring unit, corresponding to one pixel, can also be reduced.

It is further possible to configure the photon measuring unit to have a count adder 303*a* that is provided for every detector pixel such as 0101. The count adder 303*a* adds counting results outputted from the plural photon measuring circuits (P) 301*a* to 301*i*, respectively connected to the detector elements (D) 0101*a* to 0101*i* that constitute one detector pixel 0101. With this configuration, a count value of photons as to one detector pixel 0101 can be obtained at a desired measuring velocity.

Figure 4:
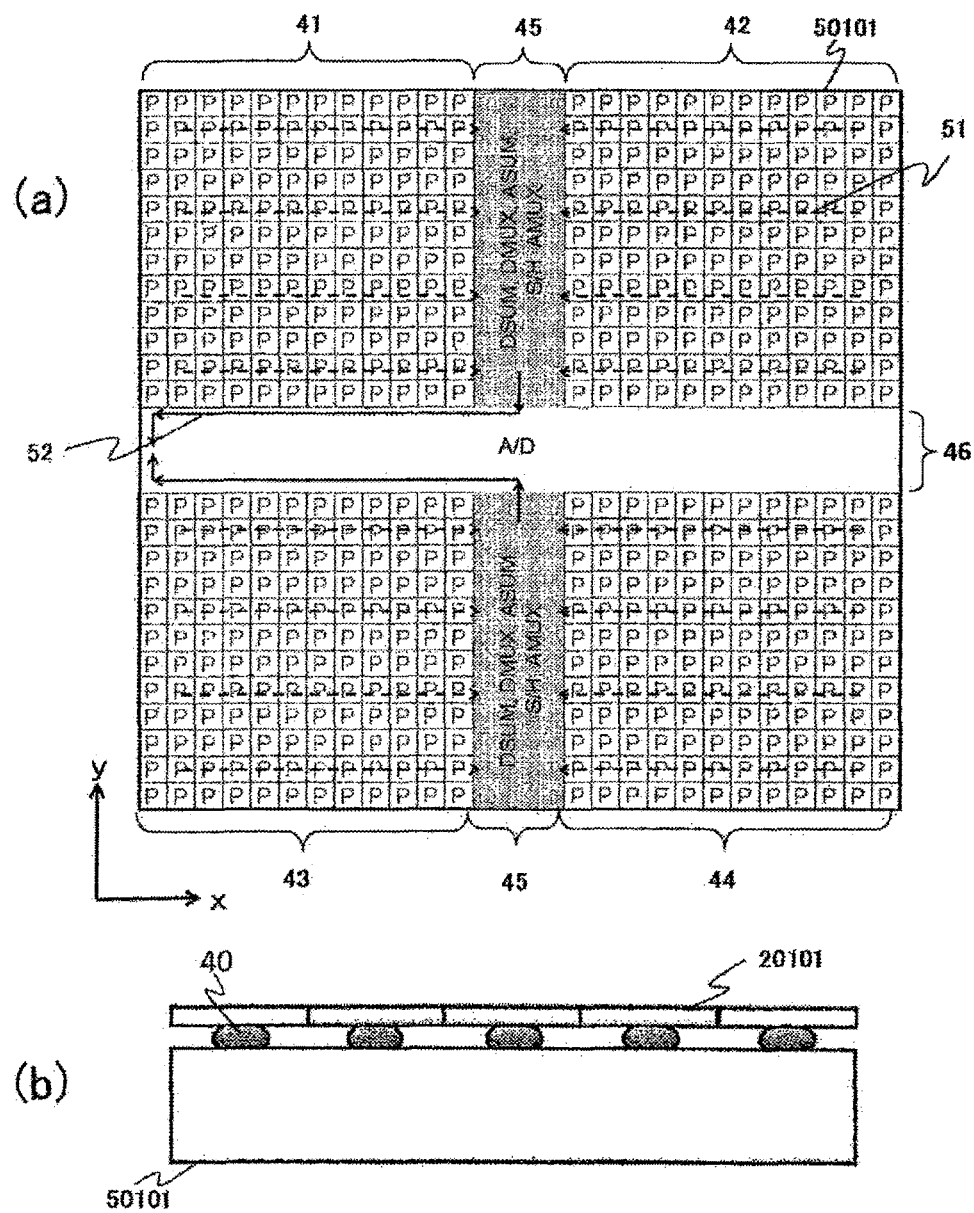
FIG. 4(a) illustrates a layout in a circuit substrate according to the first embodiment.
FIG. 4(b) is a cross sectional view of the detector element substrates and the circuit substrate being laminated.

It is desired that the plural detector elements (D) be mounted on the detector element substrate 20101, in a specified array as shown in FIG. 2. In addition, it is also desired that the photon measuring unit and the current measuring unit be mounted on a circuit substrate 50101 being an LSI as shown in FIG. 4(*a*). When the circuit configuration of the photon measuring unit and the current measuring unit of the present embodiment is employed, a total of the circuit areas of the photon measuring unit and the current measuring unit can be equivalent to or less than the area of the detector elements (D) in the array as shown in FIG. 2(*a*). Therefore, the area of the circuit substrate 50101 can be equivalent to or less than the area of the detector element substrate 20101, and both substrates can be arranged, being superimposed one on another as shown in FIG. 4(*b*). With this configuration, it is possible to provide the radiation detection device that performs both the photon measurement and the current measurement, without increasing the size of a conventional radiation detection device for performing the photon measurement or the current measurement.

In addition, as shown in FIG. 4(*b*), the circuit substrate 50101 and the detector element substrate 20101 being in the equivalent size, are arranged in a manner superimposed one on another, whereby a length of wiring for connecting the detector elements with the photon measuring circuits can be reduced to a length approximately corresponding to a thickness of the substrates. This configuration allows implementation of the circuit that performs both the photon measurement and the current measurement, while maintaining the operation of the photon measuring unit, which has a short time-constant and requires a high-speed measuring velocity. Even in the case where the current measuring unit is arranged with giving a higher priority on a wiring length of the circuit of the photon measuring unit, the current measuring unit can be placed on the identical circuit substrate 50101 with the photon measuring unit, and therefore, the wiring length to reach the S/H circuit 304*a* from the detector elements (D) via the integrator+adder 302*a*, and the like, can be short enough to achieve a target measuring velocity. Accordingly, the measuring velocity required by the current measuring unit can be maintained. In other words, the time constant of the operation of the photon measuring circuit may be set to be shorter than the time constant of operation of the S/H circuit 304*a* in the current measuring unit.

The photon measuring unit may further be configured to have an output selector (digital multiplexer) 308, provided for plural detector pixels such as 0101. The digital multiplexer 308 selectively delivers outputs from the count adders such as 303*a* that are provided for plural detector pixels (D) such as 0101 respectively. With this configuration, the count results of any of the detector pixels are selectively transferred to an arithmetic unit, sequentially, for reconstructing an image as described in the following, thereby allowing a photon measurement image to be reconstructed.

Similarly, an analogue multiplexer 309 can be placed between the A/D converter 310 in the current measuring unit and the S/H circuits such as 304*a* respectively for the plural detector pixels such as 0101. With this configuration, a current integral value of any of the detector pixels such as 0101 is selectively transferred to the A/D converter 310, sequentially, allowing the A/D converter to convert the transferred values, and then a conversion result is passed to the arithmetic unit for image reconstruction as described below, thereby allowing a current measurement image to be reconstructed.

As described so far, in the present embodiment, when the photon measurement data and the current measurement data are acquired as to the detector pixel, the unit of counting is set in association with the operation-time constants respectively of the photon measuring unit and the current measuring unit. In other words, for the photon measuring circuit having a small operation time constant, measurement is performed on the sub pixel (detector element (D)) basis in order to minimize the unit of counting as to the pixel, whereas for the current measuring unit having a large operation time constant, measurement is performed setting the unit of counting to be larger (e.g., n=9). In this case, as for the current measuring unit, the integrator+adder such as 302a is provided for binding the outputs per pixel, thereby enabling the unit of counting to be large (e.g., n=9). Since the unit of counting for the pixel is configured as described above, practical photon measuring performance and current measuring performance can be achieved at a low cost. Now, more specific description will be provided.

With reference to FIGS. 1 to 4 and other figures, a configuration of the radiation detection device of the first embodiment will be described more specifically. This radiation detection device is an AD conversion system that counts the number of pulses and measures a peak value, according to outputs from the detector elements that receive radiation photons and generate electric charges and deliver current pulse signals, being capable of outputting count results (count values) in the form of digital signals with respect to each pixel, and further, the system is also capable of integrating the current pulse signals from the detector elements and thereafter outputting current data that has been converted to digital signals, on a pixel by pixel basis. In the following, there will be described a case where X-rays are used as the radiation, but the radiation of the present invention is not limited to X-rays, but it may be other radiation, such as gamma rays, and proton beams.

One detector pixel 0101 comprises n (n=9, in this example) detector elements (D) 0101a to 0101i. Each of the other detector pixels 0102, 0103, 0201, 0202, 0203, . . . comprises n detector elements (D), similar to the detector pixel 0101. In addition, a configuration where k detector pixels 0101, 0102, . . . 0108, 0201, 02020 . . . 0208, 0801, 0802, . . . 0808 (k=8×8=64) are arranged represents the unit of AD conversion processing (detector element substrate) 20101 in the present embodiment (see FIG. 2(a)). Each of the other detector element substrates 20102, 20201, and 20202 has the same configuration. As shown in FIG. 2(b), it is also possible to configure an array by arranging a plurality of detector element substrates. In this example here, it is described that n (=9) detector elements constitute one pixel, and k (=64) pixels constitute the unit of AD conversion processing. However, from the viewpoints of manufacturing and creating detector elements and LSI, any other optimum quantity ratio may be selected appropriately. Further alternatively, the plurality of detector element substrates such as 20101 may be constructed as a single piece.

Here, each of the detector element (D) 0101a and others, has a pair of electrodes placing a semiconductor layer such as cadmium zinc telluride (CZT) and cadmium telluride (CdTe) therebetween, and when x-ray photons are entered into the semiconductor layer, an electric charge occurs in the semiconductor layer, causing the detector element (D) to output current pulse signals, the number of which corresponds to the number of photons. In addition, the amount of current is approximately proportional to the energy that is given to the semiconductor layer by the photons.

Next, with reference to FIG. 4(a), a circuit configuration of the circuit substrate 50101 will be described, which performs signal processing on the unit of AD conversion process (detector element substrate). A block 305a for performing signal processing on the outputs from n detector elements (D) 0101a to 0101i in one detector pixel such as 0101, incorporates the charge amplifier circuits (A) 313a to 313i, the photon measuring circuits (P) 301a to 301i, the count adder 303a, the integrator+adder 302a, and the sample-hold circuit (S/H) 304a. Other blocks such as 305b have the same configuration, respectively associated with other detector pixels such as 0102. One digital multiplexer 308, one analogue multiplexer 309, and one A/D converter 310, are provided for k (=64) blocks such as 305a.

The detector elements (D) 0101a to 0101i are connected, to the photon measuring circuits (P) 301a to 301i on a one-to-one basis, via wiring W301a to W301i, The charge amplifier circuits (A) 313a to 313i are placed between the detector elements (D) such as 0101a and the photon measuring circuits (P) such as 301a, so as to perform charge-voltage conversion. In addition, it is preferable to provide space (not illustrated) between the charge amplifier circuits (A) and the proton counting circuit (P) to constitute a high-pass filter for waveform shaping.

Simultaneously, the detector elements (D) 0101a to 0101i and the charge amplifier circuits (A) 313a to 313i are connected to the integrator+adder 302a, in n-to-1 correspondence via the wirings W302a to W302i. In other words, output wirings of the charge amplifier circuits (A) 313a to 313i branch into the wirings W301a to W301i and the wirings W302a to W302i, and they are connected to the photon measuring circuits (P) 301a to 301i and to the integrator+adder 302a, respectively. The space for configuring the aforementioned high-pass filter is placed closer to the photon measuring circuit (P), relative to the blanch position.

The photon measuring circuits (P) 301a to 301i count the number of the voltage pulse signals respectively outputted from the charge amplifier circuits (A) 313a to 313i, and output the count results in the form of digital signals. The count results are inputted through the wirings W303a to W303i into the count adder 303a, one count adder being provided for every pixel, and the count results are added up. Kith this configuration, the total number of the photons inputted in one pixel that is divided and detected by n detector elements (D) is calculated by the count adder 303a.

On the other hand, the integrator+adder 302a adds the voltage pulse signals, keeping them as analogue signals, which are outputted from the charge amplifier circuits (A) 313a to 313i, and outputs the results to the sample-hold circuit 304a via the wiring W304a. The sample-hold circuit 304a holds the output from the integrator+adder 302a, by sample holding. Examples of the charge amplifier, the integrator, and the adder are shown in FIGS. 3(b) to 3(d), but they may be modified to other circuit configurations as appropriate.

Outputs such as 306a, 306b, and 306c of digital signals from the count adders such as 303a, 303b, and 303c that are provided respectively for k (=64) blocks such as 305a, 305b, and 305c, are inputted in one digital multiplexer 308, delivered selectively, and transferred to a reconstruction processor for a photon measurement image as described below.

On the other hand, the outputs such as 307a, 307b, and 307c from the sample-hold circuits such as 304a, 304b, and 304c that are provided respectively for k (=64) blocks such as 305a, 305b, and 305c, are inputted in one analogue multiplexer 309, and delivered selectively.

Outputs from the analogue multiplexer 309 are inputted in the A/D converter 310 via the wiring W310, converted into digital signals, and transferred to a reconstruction processor for a current measurement image, which will be described below.

Figure 5:
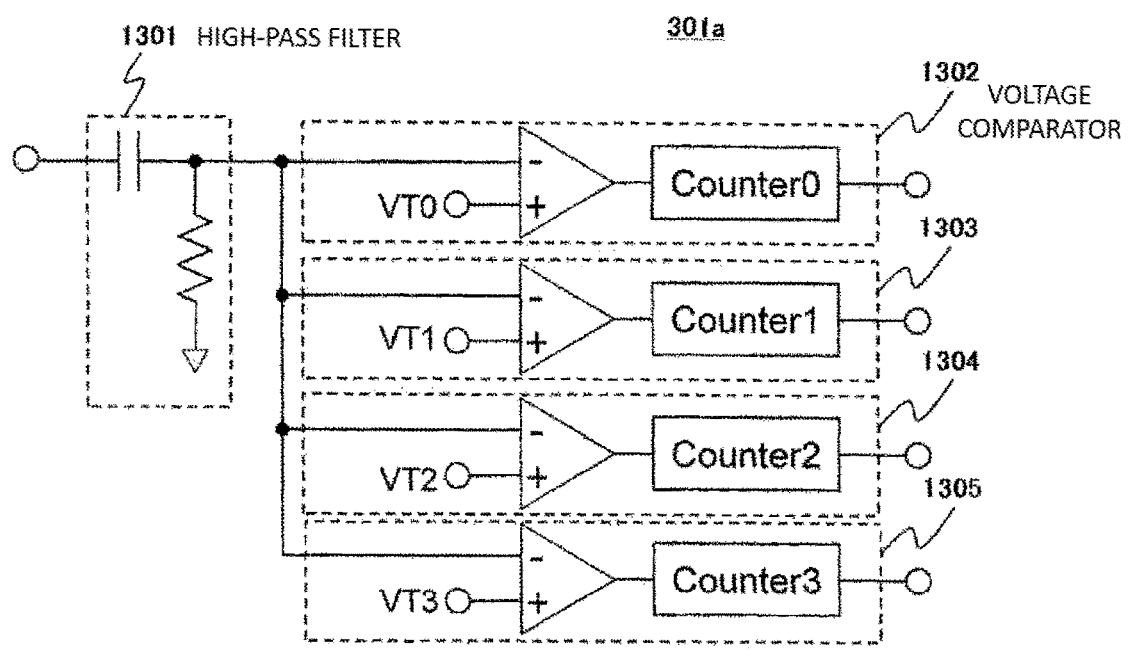
FIG. 5 is a block diagram showing a circuit configuration example of a photon measuring circuit according to the first embodiment.

Specifically, a circuit as shown in FIG. 5 may be employed as the configuration of the photon measuring circuit (P) such as 301a. That is, the photon measuring circuit (P) incorporates a high-pass filter circuit 1301 and plural voltage comparators 1302 to 1305. Then, after the high-pass filter circuit 1301 performs shaping on the voltage pulse signals outputted from the detector element such as 0101a, the voltage comparators 1302 to 1305 perform a comparison with various voltage levels, thereby measuring the number of pulses and a peak value. It is to be noted that FIG. 5 shows a circuit configuration that performs the comparison with four types of voltage, but the types of voltage may be modified as appropriate. In addition, the high-pass filter circuit 1301 may be eliminated depending on the shape of pulses.

Next, operation of the circuit as shown in FIG. 3(a) will be described. The detector element (D) such as 0101a generates an electric charge in response to a radiation amount of X-ray photons, and thus generated electric charge is outputted in the form of current pulse signals. The charge amplifier circuit (A) such as 313a receives the current pulse signals of the detector elements such as 0101a, and converts the current pulse signals to voltage pulse signals. The photon measuring circuit (P) such as 301a receives voltage pulse signals, measures the number of pulses and a peak value, and outputs a count value of digital signals. The count results (count values) of the photon measuring circuits (P) 301a and others are added by the count adder 303a. The output 306a as the addition result from the count adder 303a is a photon measurement result as to the detector pixel 0101.

On the other hand, the charge amplifier circuits (A) 313a and others are also connected to the integrator+adder 302a, and the voltage pulse signals are added up after integrated, by the integrator+adder 302a. Outputs from the integrator+adder 302a are held in the sample-hold circuit 304a, in sync with trigger signals (not illustrated) which are separately delivered from a CT system, for example.

Also in other blocks such as 305b, the same processing as in the block 305a is performed, and there are obtained digital outputs such as 306a, 306b, and 306c being results of photon measurement, and analogue outputs such as 307a, 307b, and 307c, being results of voltage addition, on a pixel by pixel basis. The outputs such as 306a, 306b, and 306c being results of photon measurement pixel by pixel, are outputted as appropriate, in the form of a signal 311 with respect to each pixel according to a control of the digital multiplexer 308, and transferred to an arithmetic processor for reconstructing a photon measurement image in the CT system, for instance. The analogue outputs 307a, 307b, and 307c being results of voltage addition are selectively inputted in the A/D converter 310 through the analogue multiplexer 309, converted into digital signals, outputted in the form of the signal 312, pixel by pixel as appropriate, and transferred to an arithmetic processor for reconstructing a current measurement image in the CT system, for instance.

As described above, in the present embodiment, the photon measuring circuit with a small operation time constant performs counting in units of sub-pixels, being smaller than pixels, whereas the current measuring circuit (A/D converter 309) with a large operation time constant performs measurement in units of pixels. With this configuration, it is possible achieve practical photon measuring performance and current measuring performance at low cost, as calculated in the following.

Firstly, n (=9) photon measuring circuits 301a to 301i are provided for one pixel (1 mm²). In the photon measuring circuit 301a, the photon measuring performance is assumed as 50M photons/mm²/sec and the circuit area is assumed as 0.09 mm², in the currently optimized design. If nine photon measuring circuits such as 301a are provided, the photon measuring performance is 50M×9=450M photons/mm²/sec, and its area is 0.09 mm²×9=0.81 mm²/pixel, in the entire photon measuring circuits 301a to 301i.

On the other hand, the A/D converter 310 accounts for most of the area of the current measuring circuit, assuming the circuit area is 6 mm², the measurement precision is 20 bits, and the measuring velocity is around 200 k sample/sec. Since one A/D converter 310 is provided for k (=64) pixels (64 mm²), the measurement precision is 20 bit, the measuring velocity 200 k/64=3.1 k sample/sec, and its area is 6 mm²/64=0.09 mm²/pixel. Therefore, the total area of the photon measuring circuit and the current measuring circuit is approximately 0.9 mm²/pixel, and the circuit area is small enough, being equivalent to or less than the pixel size. In addition, the target performance for practical use as a CT system is achieved, that is, the photon measuring performance is equal to or higher than 450M unit/mm²/sec, and the current measuring performance, that is, the measurement precision equal to higher than 20 bits and measuring velocity equal to or higher than 3 k sample/sec.

Figure 6:
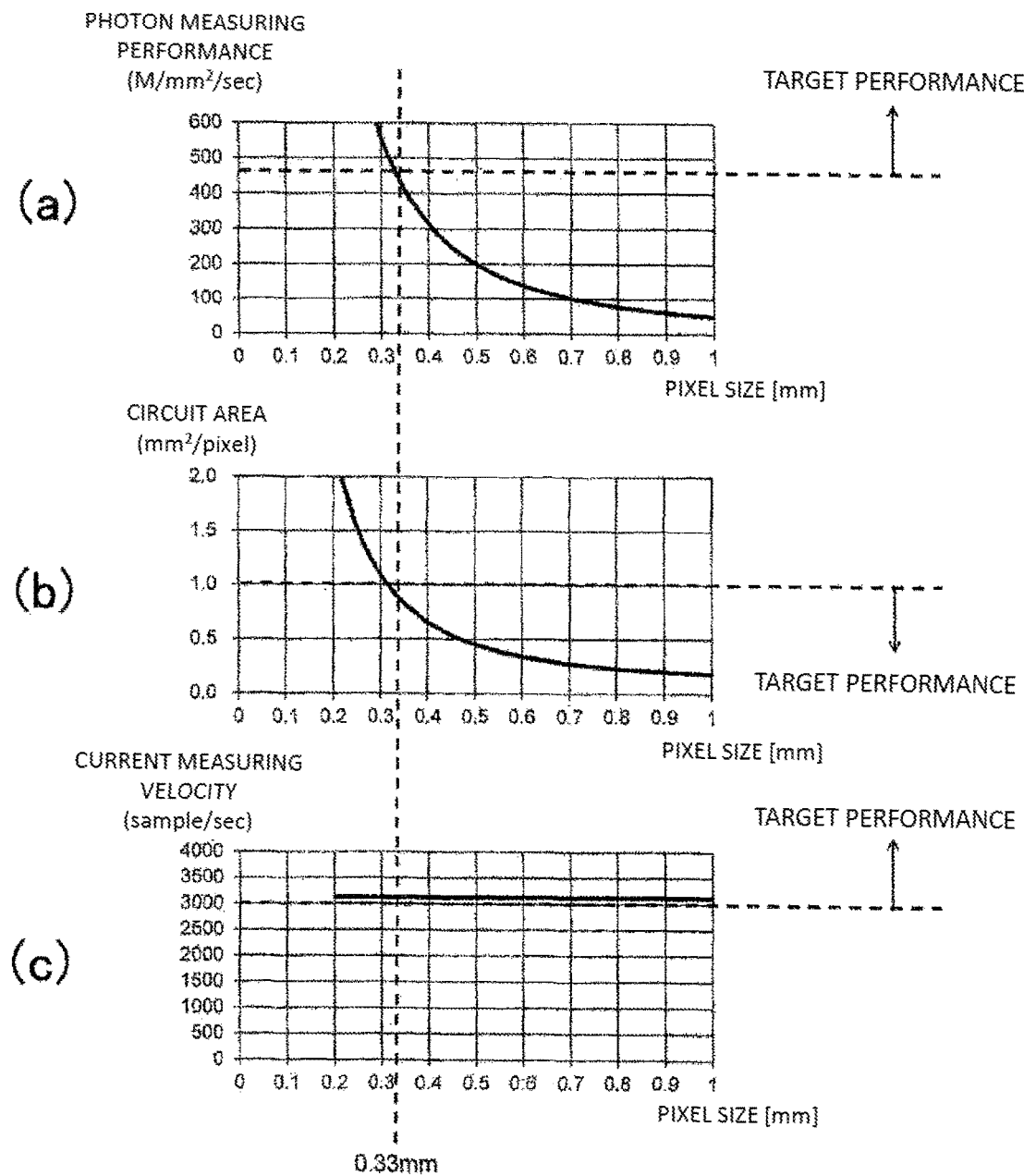
FIG. 6(a) is a graph showing a relationship between photon measuring performance and a pixel size.
FIG. 6(b) is a graph showing a relationship between a circuit area and the pixel size.
FIG. 6(c) is a graph showing a relationship between a current measuring velocity and the pixel size.

FIGS. 6(a) to 6(c) are graphs where relationships between each of the photon measuring performance, the circuit area, and the current measuring velocity, and the detector element size, are estimated according to the following formulas (1) to (3). The circuit performance and the area used in the calculation follow the aforementioned assumption, where the area of the photon measuring circuit is 0.09 mm² per piece, and the counting performance is 50M photons/mm²/sec per piece. On the other hand, it is assumed that the circuit area of the current measuring circuit is 6 mm², the precision is 20 bits, and the measuring velocity is 200 k sample/sec.

The photon measuring performance FP is expressed by the following formula (1), assuming the pixel size is D (mm).

$$FP=1/D^2\times 50 \text{ (M photons/mm}^2\text{/sec)} \tag{1}$$

In addition, as for the circuit area S per pixel, the photon measuring circuit area is 0.09 mm² per piece, and the current measuring circuit area is 6 mm². However, since the current measuring circuit is shared by 64 pixels, the circuit area is 0.094 mm²/pixel, and thus the circuit area S per pixel is expressed by the following formula (2).

$$S=1/D^2\times 0.09+0.094 \text{ (mm}^2\text{/pixel)} \tag{2}$$

As for the measuring velocity FI of the current measuring circuit, the following formula (3) is maintained to be applicable to any detector element size, since the integrator+adder 302a are provided and the measurement is performed on a pixel by pixel basis, not in units of detector elements (D) being sub-pixels.

$$FI=200\text{ k}/64=3.1\text{ k sample/sec} \quad (3)$$

As seen from FIGS. 6(a) to 6(c), the size of the detector element (D) is set to around 0.33 mm, and the photon measurement is performed in units of detector elements, while the current measurement is performed in units of pixels, thereby achieving the target performance (the circuit area is equal to or less than 1 mm²/pixel, the photon measuring performance is equal to or higher than 450M photons/mm²/sec, and the current measuring velocity is equal to or higher than 3 k sample/sec).

On the other hand, as a comparison example 1, it is assumed that one pixel is divided into nine sub-pixels, each being 0.333 mm square. Then, one photon measuring circuit (P) such as 301a is provided for one sub-pixel, and the A/D converter 310 is provided in such a manner that it is shared by 64 pixels (sub-pixels of 64 pixels*9), without placing the integrator+adder 302a. In this case, the total of the circuit areas of the photon measuring circuit (P) and the A/D converter 310 is 0.90 mm²/pixel, the photon measuring performance is 450M photons/mm²/sec. As for the current measuring performance, it can be maintained to the precision of 20 bits, but since the pixel is divided into nine sub-pixels, the measuring velocity is lowered to 0.34 k sample/sec. Therefore, the target performance of the current measurement cannot be attained.

As another comparison example 2, in order to satisfy the current measuring velocity of the target performance in the comparison example 1, when the number of A/D converters 310 is increased by nine times, the total of the circuit area is 1.65 mm²/pixel, the photon measuring performance is 450M photons/mm²/sec, and as for the current measuring performance, the precision is 20 bits and the current measuring velocity is 3.1 k sample/sec. Therefore, the target performance of the current measuring velocity can be satisfied, but in this case, it is found that the total of the circuit area does not satisfy the target performance.

As described above, in the configuration of the present embodiment, it is possible to achieve the target performance of each of the photon measuring performance and the current measuring performance. However, in order to implement such performance practically, it is necessary to reduce a wiring length to a value equal to or less than a predetermined value. There will now be described constraints of acting speed and wiring distance in the photon measuring circuit and in the current measuring circuit. In general, RC time constant $\tau$ of signal propagation can be expressed by the following formula (4), where circuit wiring distance is L (mm), parasitic wiring capacitance is $C_{para}$ (pF/mm), and parasitic wiring resistance is $R_{para}$ ($\Omega$).

$$\tau = C_{para} \times R_{para} \times L^2 \quad (4)$$

Therefore, assuming that RC time constant permitted by the photon measuring circuit (P) is $\tau_P$ (second), and the RC time constant permitted by the current measuring circuit (the integrator+adder 302a, the sample-hold circuit 304a, the analogue multiplexer 309, and the A/D converter 310) is $\tau_I$ (second), the wiring lengths $L_P$ and $L_I$ permitted by those circuits are expressed by the following formulas (5) and (6), respectively.

$$L_P \propto \sqrt{\tau_P} \quad (5)$$

$$L_I \propto \sqrt{\tau_I} \quad (6)$$

In other words, the wiring length permitted by the circuit is proportional to the square root of the circuit time constant. In here, assuming that the RC time constant of the photon measuring circuit (P) is 20 nsec, and the RC time constant of the current measuring circuit (the integrator+adder 302a, the sample-hold circuit 304a, the analogue multiplexer 309, and the A/D converter 310) is 5 $\mu$sec, the wiring lengths $L_P$ and $L_I$ permitted by the respective circuits are calculated, resulting in that the ratio between the maximum wiring lengths is 1:16.

A relationship between the RC time constant and the wiring distance will be described by more specific example as the following. When the counting performance of the photon measuring circuit (P) is assumed as 50M photons/sec, the circuit operation time per photon is 20 nsec, and when the counting performance of the current measuring circuit is assumed as 200 k sample/sec, the circuit operation time per sample is 5 $\mu$sec. If the time allocated to signal propagation in each circuit operation time is 5%, the signal propagation time permitted by the photon measuring circuit is 1 nsec, and the signal propagation time permitted by the current measuring circuit is 250 nsec.

When the parasitic wiring capacitance is assumed as 0.3 pF/mm and the parasitic wiring resistance is assumed as 300 $\Omega$/mm, which are parasitic components within the circuit substrate, the time of 5$\tau$ that makes a deviation from final static voltage to be 0.7% is expressed by:

$$0.3 \text{ (pF/mm)} \times 300 \text{ }(\Omega/\text{mm}) \times (\text{wiring length})^2 \times 5$$

For example, when the wiring length is 1 mm, the time is 0.45 nsec, when the wiring length is 2 mm, the time is 1.8 nsec, when the wiring length is 10 mm, the time is 45 nsec, and when the wiring length is 20 mm, the time is 180 nsec. Therefore, the wiring length permitted by the photon measuring circuit (P) is short, around 1.5 mm, whereas the wiring length permitted by the current measuring circuit is longer, such as exceeding 20 mm. Accordingly, when the wiring length between the detector elements (D) such as 0101a and the photon measuring circuits (P) such as 301a is restricted to within 1.5 mm, and considering operations of each circuit in the current measuring circuit, the wiring length between the detector elements such as 0101a and the sample-hold circuits such as 304a is restricted to within 20 mm, and the wiring length between the sample-hold circuits such as 304a and the A/D converter 310 is restricted to within 20 mm, it is possible to attain target performance or higher performance with regard to the acting speed of the photon measuring circuit and the current measuring circuit.

It is to be noted that the relationship between the operation time constant of the circuits and the permissible maximum wiring length has been described with specific numerical values. However, those constraints and specific numerical values may vary within a certain range, depending on a manufacturing process of the circuit substrate (LSI chip) and its drive current, and therefore, it is needless to say that they may be modified as appropriate to the extent that circuit operations will not be hampered.

As described above, in the present embodiment, since the circuit area is equal to or less than the pixel area, it is possible to make the circuit substrate 50101 to have the area equal to or less than the area of the detector element substrate 20101, and the circuit substrate 50101 and the detector element substrate 20101 can be superimposed one on another as shown in FIG. 4(b), connected via bumps 40, or the like. With this configuration, the detector elements (D) such as 0101a and the photon measuring circuits (P) such as 301a being connected, are placed in the positions in approximately a one-to-one relationship in a substrate thickness direction, thereby reducing the length of the wirings W301a to a length substantially corresponding to the thickness of the substrate 20101, enabling the wiring length to be within 1.5 mm. On the other hand, since it is only required that the wiring length between the detector elements such as 0101*a* and the sample-hold circuits such as 304*a* should be within 20 mm, and the wiring length between the sample-hold circuits such as 304*a* and the A/D converter 310 should be within 20 mm, they can be placed relatively freely on the circuit substrate 50101.

There will now be described a specific layout example within the circuit substrate 50101 having the circuit configuration as shown in FIG. 3(*a*). FIG. 4(*a*) shows the layout of circuit substrate 50101 for processing outputs from each of the detector elements (D) such as 0101*a* in the detector element substrate 20101 having 8×8 pixels as shown in FIG. 2. There are mounted 64 blocks such as 305*a*, 305*b*, and 305*c* as shown in FIG. 3(*a*) on the circuit substrate 50101. In other words, there are 576 detector elements (D) in total on the detector element substrate 20101, where 8×8=64 pixels are mounted, each pixel including 3×3=9 sub-pixels (detector elements (D)). The 576 detector elements (D) are connected respectively to the same number of photon measuring circuits (P) which are mounted on the circuit substrate 50101, together with 64 count adders (DSUM) such as 303*a*, integrators+adders (ASUM) such as 302*a*, and sample-hold circuits (S/H) such as 304*a*, one digital multiplexer (DMUX) 308, one analogue multiplexer (AMUX) 309, and one A/D converter 310.

In the layout as shown in FIG. 4(*a*), regions 41 to 44 are provided, respectively on the four corners of the circuit substrate 50101, and there are arranged 144 (576/4) photon measuring circuits (P) on each of the four regions. In addition, there are also band-like regions 45 and 46 between the four regions, and there are arranged the count adders (DSUM) such as 303*a*, the integrators+adders (ASUM) such as 302*a*, the sample-hold circuits (S/H) such as 304*a*, the digital multiplexer (DMUX) 308, and the analogue multiplexer (AMUX) 309 in the region 45 being long in the y-direction, whereas there is arranged the A/D converter 310 in the region 46 being long in the x-direction.

Since the detector element substrate 20101 is provided in a superimposed manner on the circuit substrate 50101, the photon measuring circuits (P) having small time constant lie substantially just under the detector elements (D), and located extremely close thereto, corresponding to the thickness of the detector element substrate 20101 and the thickness of the bump 40. Therefore, it is possible to achieve closer distance, making the wirings W301*a*, W301*b*, . . . W301*i* shorter, which connect the detector elements (D) such as 0101*a* with the photon measuring circuits (P) such as 301*a*.

In addition, channels of the wirings W302*a* to W302*i* connecting the detector elements (D) with the integrator+adder (ASUM) 302*a*, and of the wirings W303*a* to W303*i* connecting the photon measuring circuits such as 301*a* with the count adder (DSUM) 303*a* as shown in FIG. 3(*a*), are roughly depicted as the lines 51 shown in FIG. 4(*a*). Since the A/D converter circuit 310 having a large time constant and a large circuit area is placed in the region 46, the channel of the wiring W310 connecting between the analogue multiplexer (AMUX) 309 and the A/D converter 310 is roughly depicted as the line 52 shown in FIG. 4(*a*).

In the layout of FIG. 4(*a*), the analogue circuits such as the integrator+adder (ASUM) 302*a*, the sample-hold circuit (S/H) 304*a*, and the analogue multiplexer (AMUX) 309, are collectively arranged within the region 45, and therefore, there are advantages that circuit functions such as a source of current can be shared, thereby reducing the circuit area and consumed current.

In addition, since it is desirable to keep a delay time of signal propagation from varying significantly, pixel by pixel, the wiring W310 is connected at the same distance from each pixel, as indicated by the line 52 in FIG. 4(*a*), thereby producing an effect that measuring on each pixel can be performed at the same timing.

Furthermore, the A/D converter 310 with the large area is collectively arranged in the region 46, thereby producing an effect that useless areas can be reduced in the circuit layout. In the present embodiment, the DSUM, DMUX, ASUM, S/H, and AMUX are placed in the region 45, and the A/D converter is placed in the region 46. However, it is further possible to modify the arrangement appropriately, such as placing the S/H and the A/D converter in the region 46, for instance, so as to optimize the layout.

Figure 7:
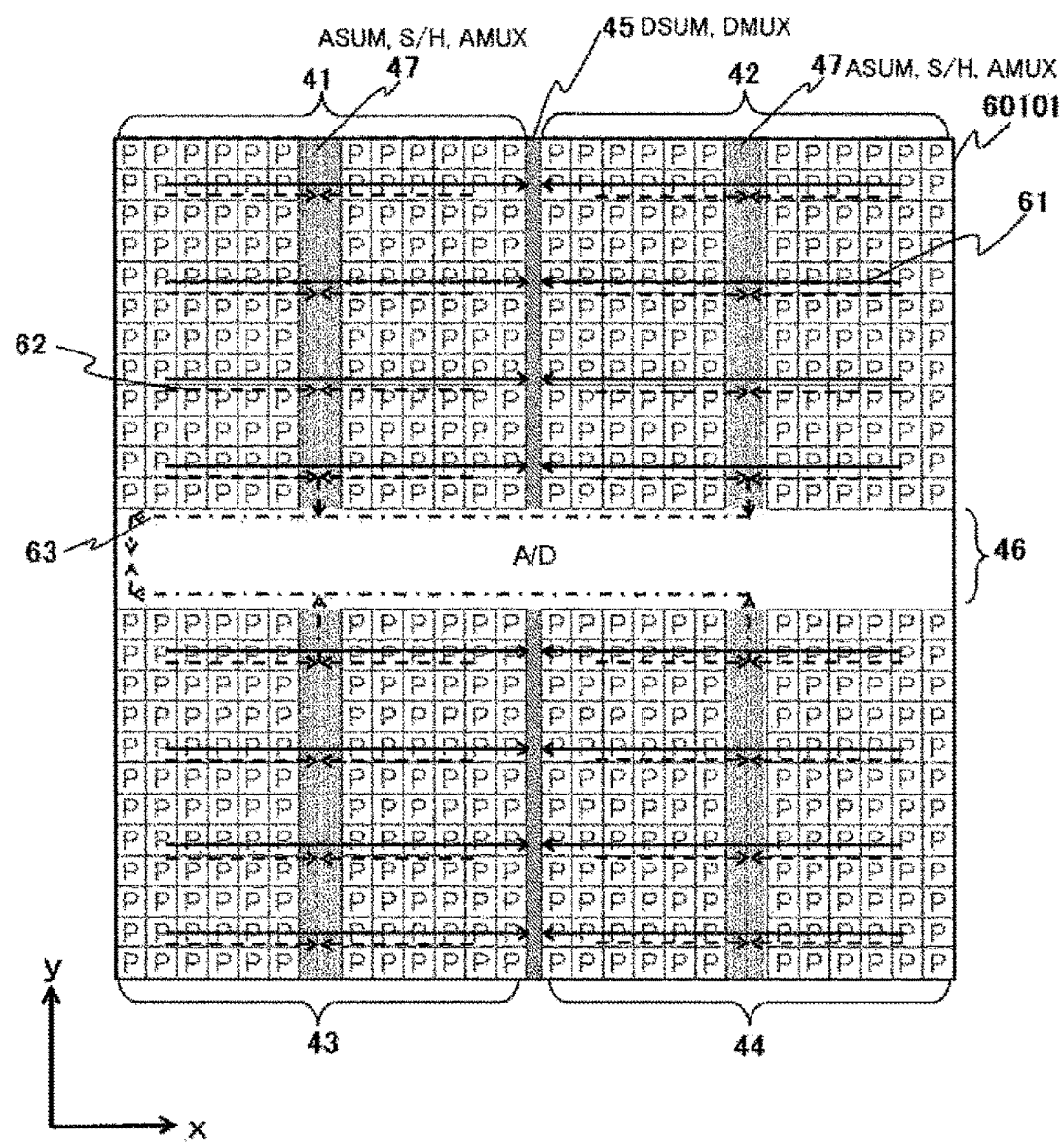
FIG. 7 illustrates another layout example in the circuit substrate according to the first embodiment.

FIG. 7 shows another layout of the circuit substrate. The circuit substrate 60101 with the layout of FIG. 7 is provided with regions 41 to 44 on the four corners of the circuit substrate 60101, and 144 (576/4) photon measuring circuits (P) are arranged on each of the four regions. This point is the same as the layout as shown in FIG. 4(*a*), but the point different from the layout of FIG. 4(*a*) is that band-like regions 47 with a predetermined width are provided along the y-direction, respectively at the centers of the regions 41 to 44. By providing the regions 47, the width of the region 45 is made narrower.

In each of the band-like regions 47 provided in the four regions 41 to 44, there are arranged plural number of integrator+adders (ASUM) such as 302*a*, sample-hold circuits (S/H) such as 304*a*, and analogue multiplexers (AMUX) 309. In the center of the region 45, there are arranged the count adders (DSUM) 303*a* and the digital multiplexer (DMUX) 308.

The lines 61 as shown in FIG. 7 roughly indicate channels of the wirings W303*a* to W303*i*, connecting the photon measuring circuits (P) such as 301*a* and the count adder (DSUM) 303*a* as shown in FIG. 3(*a*). The lines 62 as shown in FIG. 7 roughly indicate channels of the wirings W302*a* to W302*i* from the detector elements (D) such as 0101*a* to the integrator+adder (ASUM) 302*a*. The line 63 roughly indicates a channel of the wiring W310, connecting the analogue multiplexer (AMUX) 309 and the A/D converter 310.

The layout of FIG. 7 has an advantage that power supply is facilitated, since the digital-system circuits (the count adders (DSUM) such as 303*a* and the digital multiplexer (DMUX) 308), and the analogue-system circuits (the integrators+adders (ASUM) such as 302*a*, the sample-hold circuits (S/H) such as 304*a*, and the analogue multiplexer (AMUX) 309) can be separated and collectively arranged, respectively. Since the digital-system circuits and the analogue-system circuits are separated, noise mixing into the analogue-system circuits from the digital-system circuits can be reduced.

In addition, the layout in FIG. 7 has an advantage that variation of wiring distance from the detector elements (D) to the sample-hold circuits (S/H) such as 304*a* can be reduced relative to the layout as shown in FIG. 4(*a*). Also in the present embodiment, similar to descriptions with reference to FIG. 4, arranging locations may be modified as appropriate, in such a manner that the S/H and the A/D converter are arranged in the region 46, for instance.

Though not illustrate specifically, depending on the area and shape of each circuit, the layout shown in FIG. 7 may be modified in such a manner that the region 45 and the region 47 are exchanged, that is, the digital-system circuits may be arranged in the region 47, and the analogue-system circuits may be arranged in the region 45.

Figure 8:
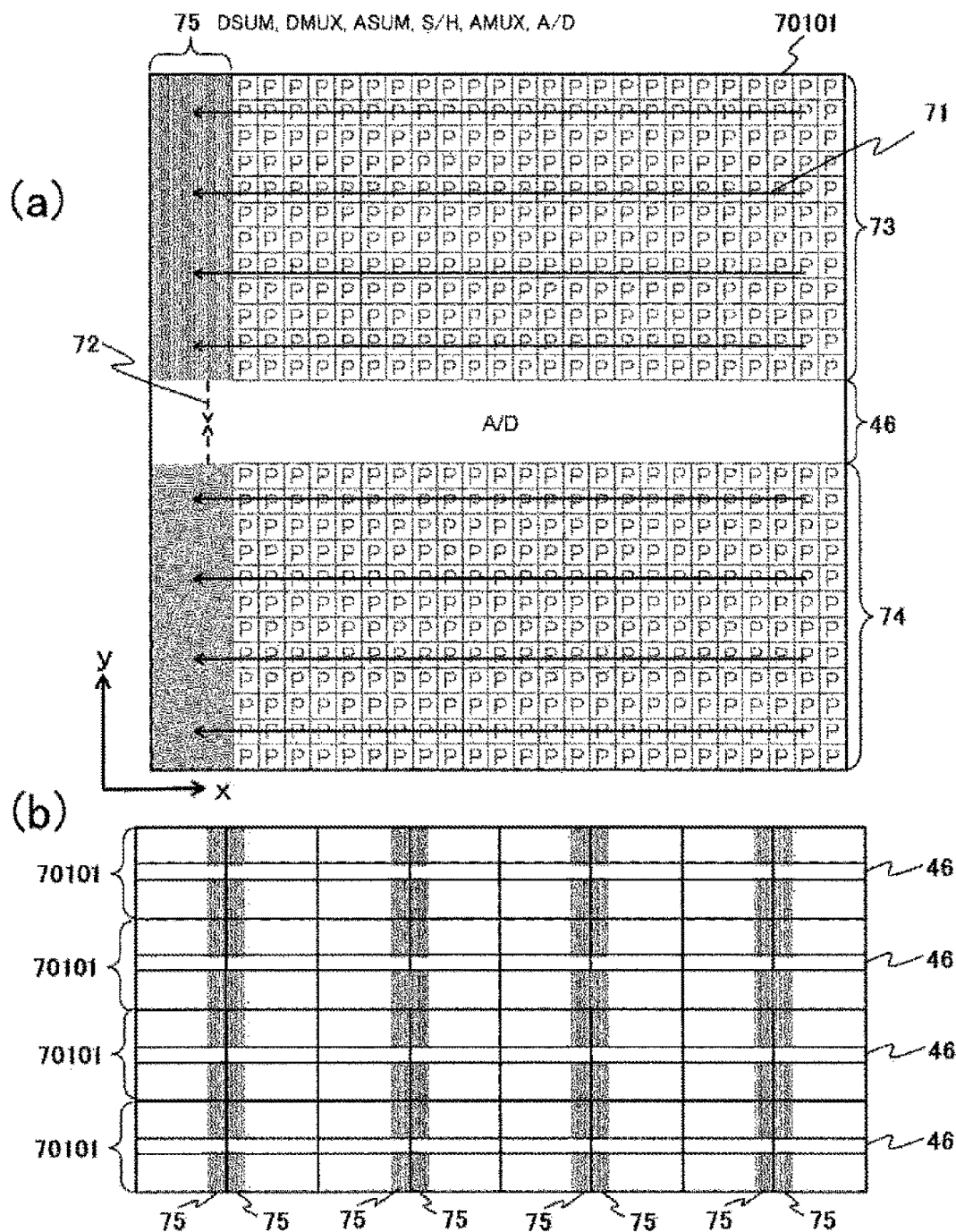
FIG. 8(a) illustrates another layout example in the circuit substrate according to the first embodiment.
FIG. 8(b) illustrates the state where the circuit substrates are arranged.

FIG. 8(a) illustrates the circuit substrate 70101 having another layout example. FIG. 8(a) illustrates the circuit substrate 70101 where 288 (=576/2) photon measuring circuits (P) are arranged in each of the upper right-side region 73 and the lower right-side region 74. There are arranged in the band-like region 75 along the y-direction on the left-edge side of the circuit substrate 70101, the count adders (DSUM) such as 303a, the integrators+adders (ASUM) such as 302a, the sample-hold circuits (S/H) such as 304a, the digital multiplexer (DMUX) 308, and the analogue multiplexer (AMUX) 305. The A/D converter 310 is arranged in the region 46 that is long in the x-direction in the center.

Unlike the layouts as shown in FIG. 4(a) and FIG. 7, the photon measuring circuits (P) are collectively arranged in the two regions 73 and 74 in the layout as shown in FIG. 8(a). The lines 71 shown in FIG. 8(a) roughly indicate channels of the wirings W303a to W303i connecting the photon measuring circuits (P) such as 301a and the count adder (DSUM) 303a, and the wirings W302a to W302i connecting from the detector elements (D) such as 0101a to the integrator+adder (ASUM) 302a. The line 72 roughly indicates a channel of the wiring W310 that connects the analogue multiplexer (AMUX) 309 with the A/D converter 310.

In the layout as shown in FIG. 8(a), the analogue system circuits (the integrators+adders (ASUM) such as 302a, the sample-hold circuits (S/H) such as 304a, and the analogue multiplexer (AMUX) 309) are collectively arranged, and circuit functions such as a source of current can be shared, thereby producing an advantage that the circuit area and consumed current can be reduced. In addition, the A/D converter 310 with a large area is collectively arranged in the region 46, thereby producing an effect that reduces useless areas in the circuit layout.

In addition, when the circuit substrates 70101 of FIG. 8(a) are arranged in an array, one of the circuit substrates 70101 being adjacent to each other in the x-direction is flipped horizontally along the x-direction as shown in FIG. 8(b), whereby the region 75 becomes adjacent to another region 75 of the neighboring circuit substrate 70101. With this configuration, there is also an advantage that power supply may be more simplified, when the circuit substrates 70101 are arranged in the array. Also in the present embodiment, similar to the descriptions with reference to FIG. 4, arranging locations may be modified as appropriate, in such a manner that the S/H and the A/D converter are arranged in the region 46, for instance.

Figure 9:
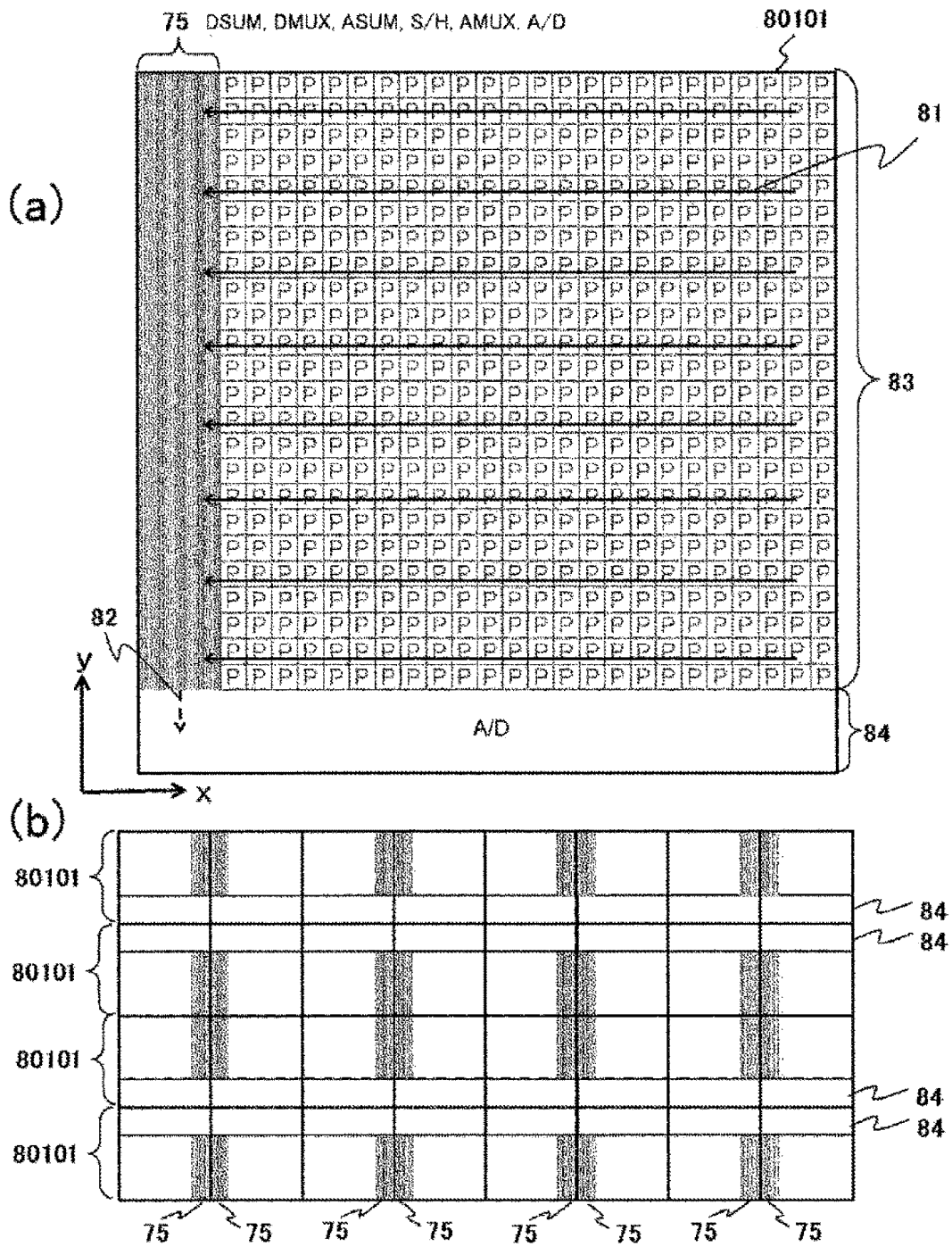
FIG. 9(a) illustrates another layout example in the circuit substrate according to the first embodiment.
FIG. 9(b) illustrates the state where the circuit substrates are arranged.

FIG. 9(a) further illustrates another layout of the circuit substrate 80101. In the layout of FIG. 9(a), a band-like region 75 is provided along the y-direction on the left edge of the circuit substrate 80101, and another band-like region is provided along the x-direction on the bottom edge of the circuit substrate 80101. Then, all the photon measuring circuits P are arranged in the region 83, other than the above band-like regions. In the band-like region 75 along the y-direction on the left edge of the circuit substrate 80101, there are arranged the count adders (DSUM) such as 303a, the integrators+adders (ASUM) such as 302a, the sample-hold circuits (S/H) such as 304a, the digital multiplexer (DMUX) 308, and the analogue multiplexer (AMUX) 309. The A/D converter 310 is arranged in the region 84 that is long in the x-direction on the bottom edge.

The lines 81 in FIG. 9(a) roughly indicate channels of the wirings W303a to W303i connecting the photon measuring circuits (P) such as 301a with the count adders (DSUM) 303a, and of the wirings W302a to W302i connecting the detector elements (D) such as 0101a and the integrator+adder (ASUM) 302a. The line 82 roughly indicates a channel of the wiring W310 that connects the analogue multiplexer (AMUX) 309 with the A/D converter 310.

In the layout as shown in FIG. 9(a), similar to the layout as shown in FIG. 8(a), since the analogue system circuits (the integrators+adders (ASUM) such as 302a, the sample-hold circuits (S/H) such as 304a, and the analogue multiplexer (AMUX) 309) are collectively arranged, the circuit functions including a source of current are shared, thereby producing an advantage that the circuit area and the consumed current can be reduced. In addition, the A/D converter 310 with a large area is collectively arranged in the region 84, thereby producing an effect that reduces useless areas in the circuit layout.

In addition, when the circuit substrates 80101 of FIG. 9(a) are arranged in an array, one of the circuit substrates 80101 being adjacent to each other in the x-direction is flipped horizontally along the x-direction, and one of the circuit substrates 80101 being adjacent to each other in the y-direction is flipped vertically along the y-direction as shown in FIG. 9(b), whereby the region 75 becomes adjacent to another region 75 of the neighboring circuit substrate 80101, and the region 84 becomes adjacent to another region 84 of another neighboring circuit substrate 80101. With this configuration, there is also an advantage that power supply may be more simplified, when the circuit substrates 80101 are arranged in the array. Also in the present embodiment, similar to the descriptions with reference to the figures such as FIG. 5, arranging locations may be modified as appropriate, in such a manner that the S/H and the A/D converter are arranged in the region 84, for instance.

It is also possible that the digital multiplexer 308 and the analogue multiplexer 309 as shown in FIG. 3(a) have multistage configurations, respectively.

The layouts as shown in FIGS. 4(a), 7, 8(a), and 9(a) are just examples of the present embodiment, and a layout orientation may be modified by flipping relative to x-axis, relative to y-axis, rotation, or the like. Furthermore, an input terminal of the A/D converter circuit 310 is located at the center of the left edge, but it may be modified as appropriate.

Second Embodiment

Figure 10:
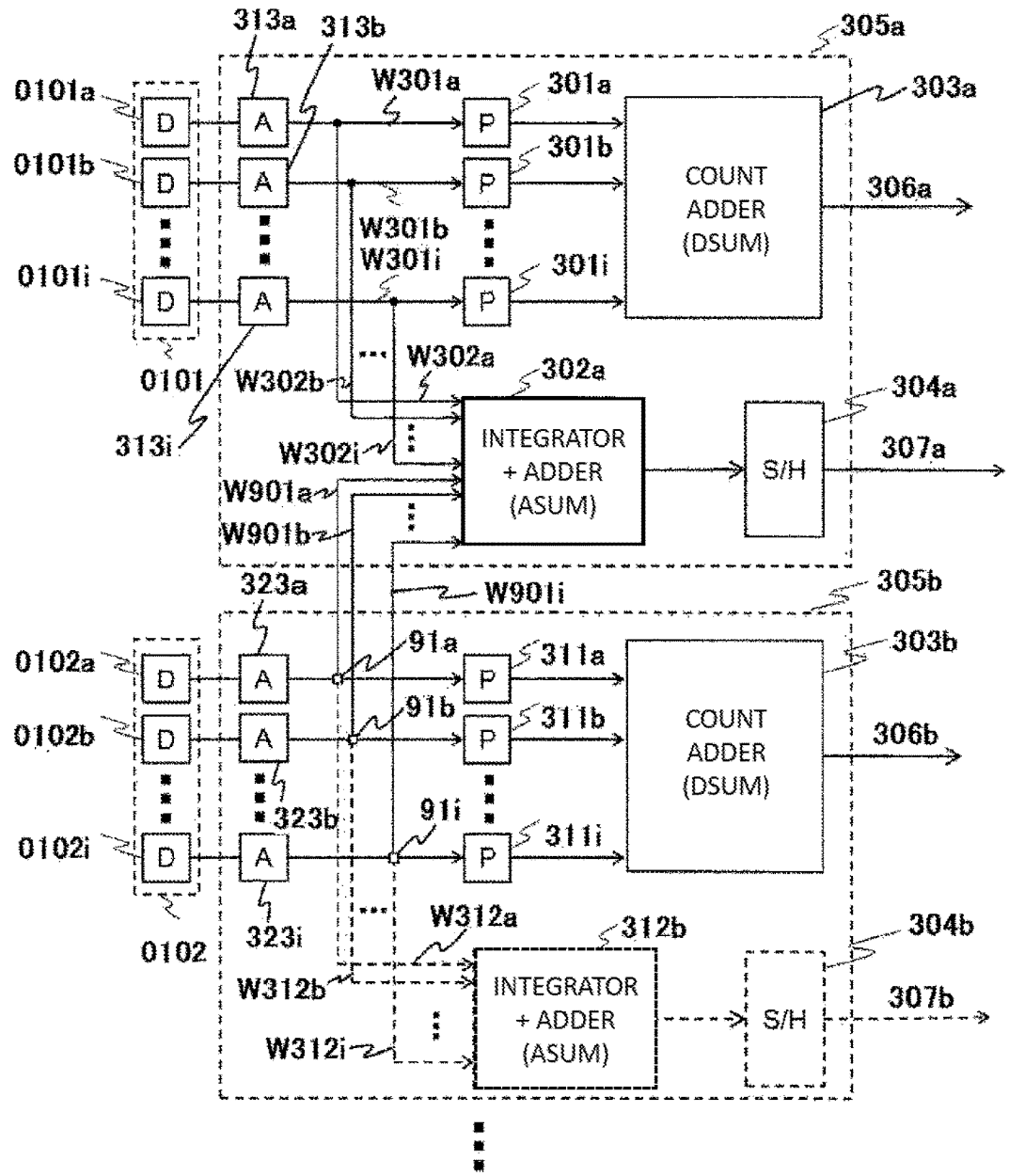
FIG. 10 is a block diagram showing a circuit configuration of the radiation detection device according to a second embodiment.

With reference to FIG. 10, the radiation detection device of the second embodiment will be described.

As shown in FIG. 10, the configuration of the measuring circuits in the radiation detection device according to the second embodiment is the same as the configuration of the first embodiment as shown in FIG. 3(a), but in the block 305b corresponding to the detector pixel 0102, the second embodiment is different from the first embodiment, in the point that not only the wirings W312a to W312i are provided but also the wirings W901a to W901i are provided; where current pulse signals from n detector elements 0102a to 0102i in the pixel 102 are converted into voltage pulse signals via the charge amplifiers (A) 323a to 323i, and the voltage pulse signals are allowed to be entered into the integrator+adder 312b via the wirings W312a to W312i, as well as entered into the integrator+adder 302a in the adjacent detector pixel 0101 via the wirings W901a to W901i.

In addition, there are provided switches 91a to 91i between the wirings W312a to W312i and the wirings W901a to W901i, respectively. By switching the switches 91a to 91i according to a control circuit not illustrated, the pulse signals outputted from the detector elements 0102a to 0102i of the detector pixel 0102 are converted to voltage pulse signals, and thereafter, it is possible to select whether the voltage pulse signals are entered in the integrator+adder 312b in the block 305b corresponding to the detector pixel 0102, or the voltage pulse signals are entered into the integrator+adder 302a in the block 305a corresponding to the detector pixel 0101.

According to the switches 91a to 91i, if the wirings W312a to W312i are selected, similar to the first embodiment, the voltage pulse signals obtained by converting the current pulse signals outputted from the detector element 0102a to 0102i via the charge amplifiers 323a to 323i are added by the integrators+adders 312b, respectively. On the other hand, according to the switches 91a to 91i, when the wirings W901a to W901i are selected, the voltage pulse signals obtained by converting the current pulse signals outputted from the detector elements 0102a to 0102i of the detector pixel 0102 via the charge amplifiers 323a to 323i are inputted into the integrator+adder 302a, together with the voltage pulse signals obtained by converting the current pulse signals outputted from the detector elements 0101a to 0101i of the detector pixel 0101. With this configuration, all of the voltage pulse signals based on the current pulse signals outputted from the detector elements 0101a to 0101i of the detector pixel 0101, and the voltage pulse signals based on the current pulse signals outputted from the detector elements 0102a to 0102i of the detector pixel 0102, are added up by the integrator+adder 302a, and outputted to the sample-hold circuit 304a.

Therefore, when a publicly known imaging is performed where measured values between pixels are added in a CT system, the current between pixels targeted for addition can be added by the integrator+adder (ASUM) 302a. With this configuration, it is possible to stop the operations of the integrator+adder (ASUM) 312b and the sample-hold circuit 304b that are associated with the detector pixel 0102, and accordingly, consumed current can be reduced.

It is to be noted that the wirings W901a to W901i and the switches 91a to 91i may also be provided to all the pixels, or the wirings W901a to W901i and the switches 91a to 91i may be provided only in the pixels with a possibility that measured values are added between plural pixels.

On the other hand, as for the photon measurement, in order to keep an amount of measurement, it is desirable to connect the detector elements (D) and the photon measuring circuits (P) on a one-to-one basis in any of the detector pixels such as 1010 and 1012, similar to the first embodiment.

Since other configurations and operations are the same as those of the first embodiment, they will not be described redundantly.

Third Embodiment

Figure 11:
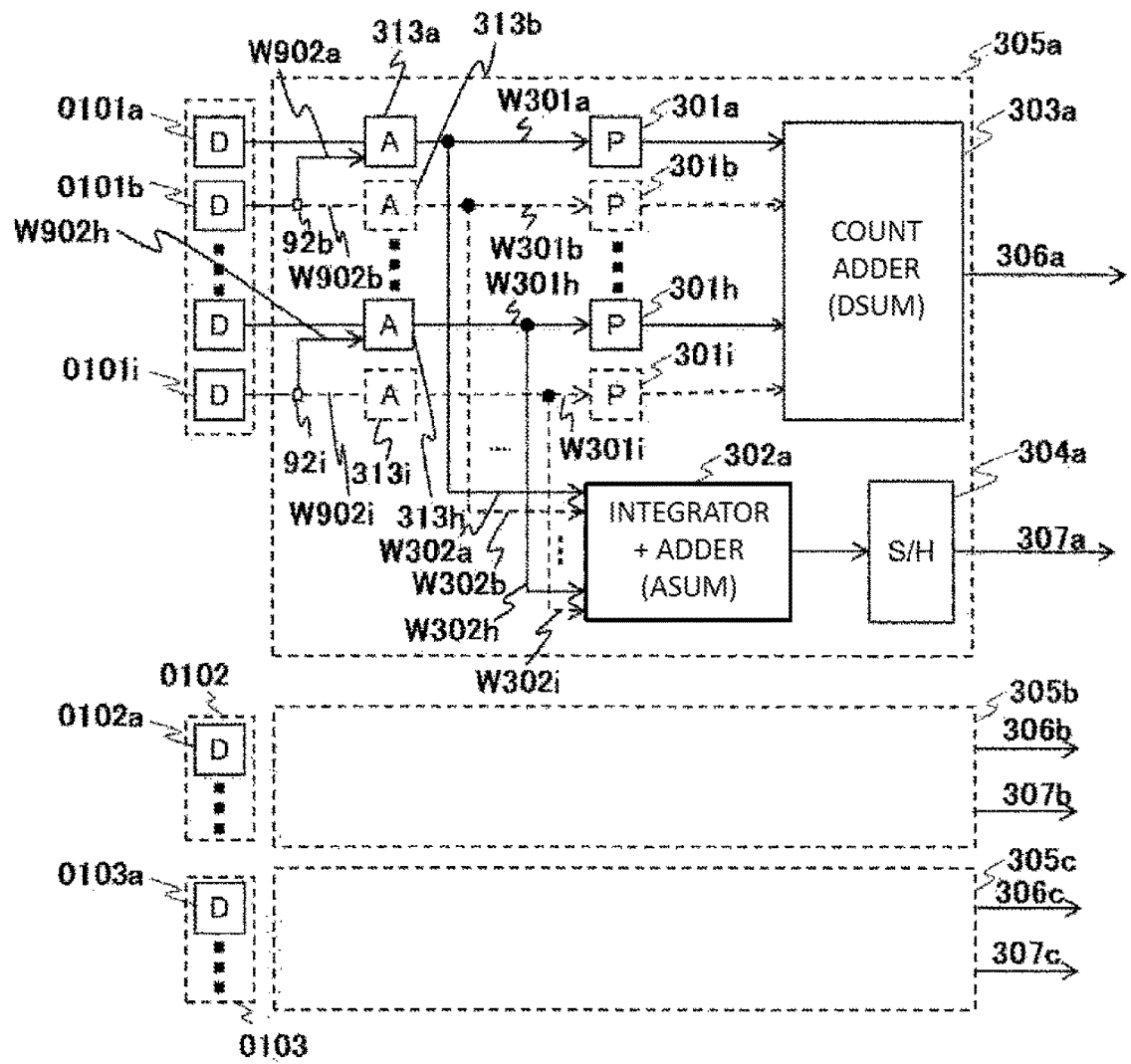
FIG. 11 is a block diagram showing the circuit configuration of the radiation detection device according to a third embodiment.

With reference to FIG. 11, the radiation detection device of the third embodiment will be described.

As shown in FIG. 11, the configuration of the measuring circuits of the third embodiment is the same as the configuration of the first embodiment as shown in FIG. 3(a), but it is different from the first embodiment in the point that half of the detector elements such as 0101b and 0101i among plural detector elements 0101a to 0101i, are connected to wirings such as W902a and W902h, respectively, which are connected to the adjacent charge amplifier circuits such as 313a and 313h, in addition to the wirings such as W902b to W902i connected to the charge amplifier circuits such as 313b and 313i.

There are provided switches 92b and 92i, between the wirings W902b, W902i and the wirings W902a, W902h, respectively. The switch 92b is switched by the control circuit, not illustrated, thereby allowing selection, either the current pulse signals outputted from the detector element 0101b are entered in the charge amplifier circuit 313b, or those current pulse signals are entered in the adjacent charge amplifier circuit 313a. Similarly, the switch 92i is switched by the control circuit, not illustrated, thereby allowing selection, either the current pulse signals outputted from the detector element 0101i are entered in the charge amplifier circuit 313i, or those current pulse signals are entered in the adjacent charge amplifier circuit 313h.

According to the selection on the switch 92b, the charge amplifier circuit 313a where the current pulse signals of the two detector elements 0101a and 0101b are entered, outputs voltage pulses obtained by adding up both current pulse signals. Similarly, according to the selection on the switches 92i, the charge amplifier circuit 313h where the current pulse signals of the two detector elements 0101h and 0101i are entered, outputs voltage pulses obtained by adding up both current pulse signals. With this configuration, if the number of current pulses entered in the photon measuring circuits such as 301a and 301h do not exceed a countable number, it is possible to count the current pulse signals outputted from all the detector elements 0101a to 0101i of the detector pixel 0101, through the photon counting circuits such as 301a and 301h, the number of which becomes almost half. The count values obtained by such counting are added up by the count adder 303a.

As described above, if the amount of irradiated X-rays is small and the number of current pulses entered in the photon measuring circuits such as 301a and 301h does not exceed the countable number, it is possible to count the current pulse signals outputted from all the detector elements 0101a to 0101i of the detector pixel 0101, by the photon measuring circuits such as 301a and 301h, the number of which is almost half. Since it is possible to stop half of the charge amplifier circuits (A) and also half of the photon measuring circuit (P), thereby reducing power consumption caused by the circuit operation. In the case where the amount of irradiated X-rays is large, photons can be counted by using all the photon measuring circuits 301a to 301i, according to selection by the switches such as 92b and 92i.

It is to be noted that in FIG. 11, there is shown an example that the detector elements (D) and the charge amplifier circuits (A) are connected on a two-to-one basis, however, if there is a mode where the number of photons to be measured is much smaller, connection on a three-to-one basis or on a four-to-one basis is also applicable.

Since other configurations and operations are the same as those of the first embodiment, they will not be described redundantly.

Fourth Embodiment

Figure 12:
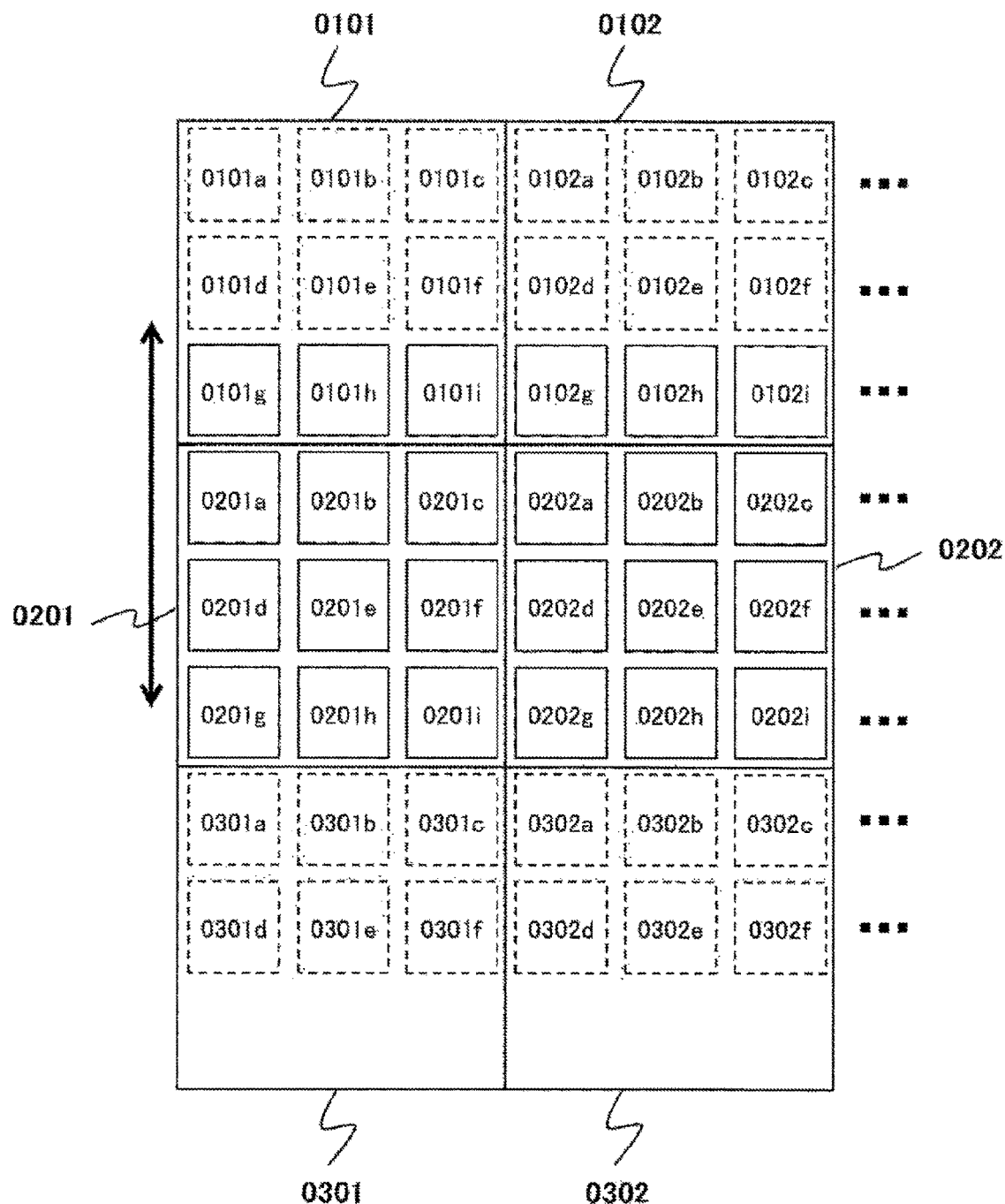
FIG. 12 illustrates an arrangement of detector elements on a detector element substrate according to a fourth embodiment.

With reference to FIG. 12, the radiation detection device of the fourth embodiment will be described.

The circuit substrate of the radiation detection device according to the fourth embodiment is the same as the circuit substrate having the layout of the first embodiment, as shown in FIGS. 4(a), 7, 8(a), and 9(a). However, as for some of the charge amplifier circuits (A) and the photon measuring circuits (P) being mounted, those operations may be stopped, in the case where the charge amplifier circuits (A)

and the photon measuring circuit (P) are connected to the detector elements (D) that are positioned outside the X-ray radiation field.

FIG. 12 illustrates an array of detector elements (D) as a part of the detector element substrate 20101. Some CT systems may employ an imaging method that sets a radiation field of X-rays to be narrower than a region of the array of the detector elements (D). In the present embodiment, the control circuit stops operations of the charge amplifier circuits (A) and the photon measuring circuits (P) that are connected to the detector elements (D) not irradiated with X-rays, thereby reducing consumed power. By way of example, the control circuit receives the X-ray radiation field, by receiving an aperture of a collimator of an X-ray generator in the CT system, or receiving the X-ray radiation field set by an operator via an operating part, identifies the detector elements located outside of the X-ray radiation field, and stops power supply to the charge amplifier circuits (A) and the photon measuring circuit (P) that are connected to thus identified detector elements (D).

By way of example, in the case of FIG. 12, operations of the charge amplifier circuits (A) and the photon measuring circuit (P) are stopped, which are connected to the detector elements (D) outside the X-ray radiation field; 0101a, 0101b, 0101c, 0101d, 0101e, 0101f, 0102a, 0102b, 0102c, 0102d, 0102e, 0102f, 0301a, 0301b, 0301c, 0301d, 0301e, 0301f, 0302a, 0302b, 0302c, 0302d, 0302e, and 0302f, thereby reducing the consumed power.

Fifth Embodiment

Figure 13:
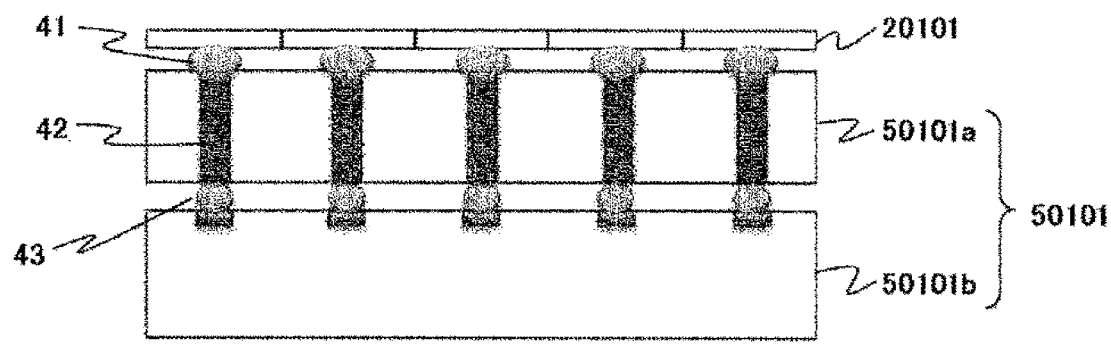
FIG. 13 is a cross sectional view of the detector element substrate and the circuit substrate being laminated according to a fifth embodiment.

With reference to FIG. 13 and other figures, a fifth embodiment will be described. In the configuration of the first to the fourth embodiments, all the circuits are mounted on the circuit substrates such as 50101, with an area equivalent to or less than the area of the detector element substrate 20101, but it is further possible to configure such that two or more circuit substrates are provided, and the circuits are divided and mounted onto the two or more circuit substrates.

As shown in FIG. 13, there are arranged two circuit substrates 50101a and 50101b, both being LSIs and superimposed one on another, under the detector element substrate 20101. The detector element substrate 20101 and the upper-side circuit substrate 50101a are connected via bumps 41. There are provided through Silicon Vias (TSVs) 42 in the thickness direction of the upper-side circuit substrate 50101. The upper-side circuit substrate 50101a and the lower-side circuit substrate 50101b are connected via the TSVs 42 and the bumps 43'.

In FIG. 13, the circuit substrate 50101a on the upper side is equipped with circuits for photon measurement (the photon measuring circuits (P) such as 301a, the count adders (DSUM) such as 303a, and the digital multiplexer (DMUX) 308), in addition to the charge amplifier circuits (A). The circuit substrate 50101b on the lower side is equipped with circuits for current measurement (the integrators+adders (ASUM) such as 302a, the sample-hold circuits (S/H) such as 304a, the analogue multiplexer (AMUX) 309, and the A/D converter 310).

As described so far, the time constant of the circuits for photon measurement is short, and the time constant of the circuits for current measurement is long. Therefore, even though the circuits for current measurement are mounted on the circuit substrate 50101b on the lower side, deterioration in circuit performance may be low.

In addition, as shown in FIG. 13, the circuits are mounted, being divided into two circuit substrates (LSI) 50101a and 50101b, this allows production of the circuit substrate 50101a equipped with the circuits for photon measurement, and the circuit substrate 50101b equipped with the circuits for current measurement, through different semiconductor process nodes, and thus there is an advantage that optimum performance for the respective circuits can be easily achieved.

In addition, since two circuit substrates 50101a and 50101b are provided separately, there is also an advantage that propagation of circuit noise can be reduced between the circuits for photon measurement and the circuits for current measurement. Furthermore, since this configuration produces more capacity in the layout areas in the respective circuit substrates 50101a and 50101b, there are advantages such as allowing those areas to be fully allocated to a power supply wiring with low impedance, and allowing those areas to be allocated to redundancy for yield enhancement, thereby achieving further performance improvement and yield enhancement of the circuits.

It should be noted that in the example of the configuration as shown in FIG. 13, the bumps 41 and 43 are used for the connection between the substrates, but different connecting means such as wire bonding may also be used as suitable.

The circuits mounted on the two circuit substrates (LSI) 50101a and 50101b may not be limited to the configuration where the circuits for the photon measurement are separated from the circuits for the current measurement as described above. By way of example, the circuit substrate (LSI) 50101a on the upper side may be configured such that the circuits for photon measurement (the photon measuring circuits (P) such as 301a, the count adders (DSUM) such as 303a, the digital multiplexer (DMUX) 308) are mounted, and in addition, the integrators+adders (ASUM) such as 302a are also mounted thereon. Other circuits (the sample-hold circuits (S/H) such as 304a, the analogue multiplexer (AMUX) 309, and the A/D converter 310) may be mounted on the circuit substrate 50101b on the lower side.

With this configuration, the layout area of the circuit substrate 50101b on the lower side grows in capacity more than the configuration as shown in FIG. 13, and thus there is an advantage the area of the circuit substrate 50101b on the lower side can be reduced.

It is also possible to configure such that the circuit substrate (LSI) 50101a on the upper side is provided with the integrators+adders (ASUM) such as 302a and the sample-hold circuits (S/H) such as 304a, in addition to the circuits for photon measurement (the photon measuring circuits (P) such as 301a, the count adders (DSUM) such as 303a, and the digital multiplexer (DMUX) 308). Other circuits (the analogue multiplexer (AMUX) 309 and the A/D converter 310) may be mounted on the circuit substrate 50101b on the lower side.

It is further possible to configure such that the circuit substrate (LSI) 50101a on the upper side is provided with the integrators+adders (ASUM) such as 302a, the sample-hold circuits (S/H) such as 304a, and the analogue multiplexer (AMUX) 309, in addition to the circuits for photon measurement (the photon measuring circuits (P) such as 301a, the count adders (DSUM) such as 303a, and the digital multiplexer (DMUX) 308). Only the A/D converter 310 may be mounted on the circuit substrate 50101b on the lower side.

Sixth Embodiment

Figure 14:
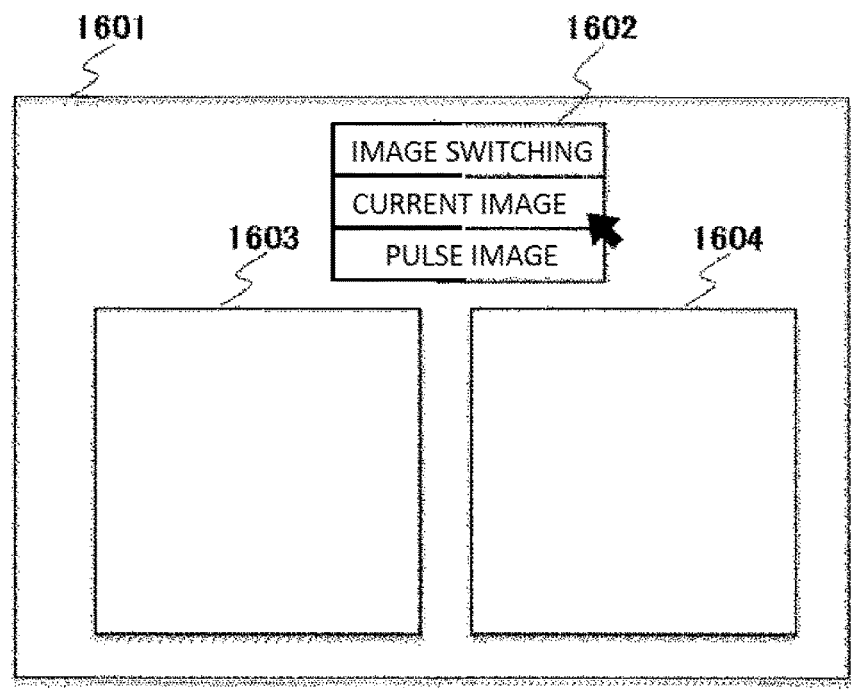
FIG. 14 illustrates a screen example according to a sixth embodiment.

With reference to FIG. 14, there will be described a display screen as a sixth embodiment, for displaying an image reconstructed based on the photon measurement data, and an image reconstructed based on the current measurement data.

In the embodiments as described so far, both of the photon measurement data and the current measured data can be acquired simultaneously, by one-time irradiation. Accordingly, as in the seventh embodiment that will be described later, it is possible to generate both a photon measurement image reconstructed based on the photon measurement data, and a current measurement image reconstructed based on the current measured data. Those images may be displayed selectively on a screen of the display unit, switched by a display controller, or may be displayed concurrently.

By way of example, the display screen 1601 as shown in FIG. 14, includes a region 1603 for displaying the current measurement image, a region 1604 for displaying the photon measurement image, and image switching icons 1602. In the image switching icons 1602, when "current image" is selected, the display controller displays the current measurement image in the region 1603, and when "pulse image" is selected, the photon measurement image is displayed in the region 1604. In addition, when both the "current image" and the "pulse image" of the image switching icons 1602 are selected, both images are displayed in the regions 1603 and 1604.

It should be noted that the arrangement and size of the regions 1603 and 1604, and the image switching icons 1602 in the display screen 1601 as shown in FIG. 14 are not limited to the configuration as shown in FIG. 14, but they may be modified as appropriate.

Seventh Embodiment

Figure 15:
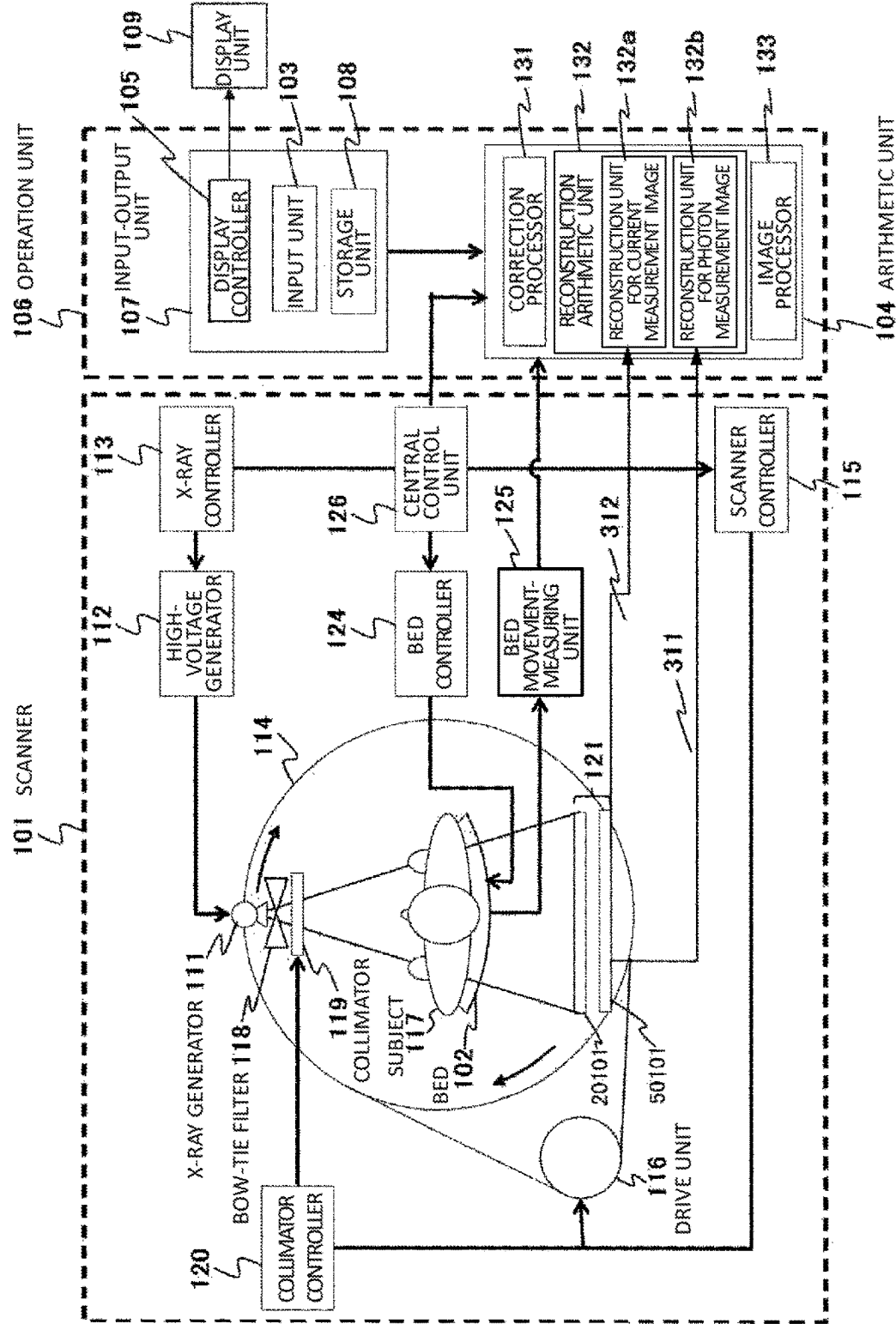
FIG. 15 is a block diagram showing a medical imaging system (CT system) according to a seventh embodiment.

With reference to FIG. 15, an example of a CT system will be described as a seventh embodiment, which is a medical imaging system provided with the radiation detection device according to any of the aforementioned first to sixth embodiment.

As shown in FIG. 15, the CT system comprises a scanner 101 used for imaging, a bed 102 that is moved with a subject placing thereon, and an operation unit 106.

The scanner 101 incorporates, an X-ray generator 111, a high-voltage generator 112, an x-ray controller 113, a radiation detection device 121, a scanner controller 115, and a central control unit 126. The high-voltage generator 112 generates predetermined current and high voltage under the control of the x-ray controller 113, and supplies the current and voltage to the x-ray generator 111. Accordingly, the x-ray generator 111 generates X-rays.

The x-ray generator 111 and the radiation detection device 121 are mounted on a disc 114 provided with an opening for sliding the subject 117 thereinto. The disc 114 is provided with a drive unit 116 for rotationally driving the disc 114. The disc 114 is also mounted with a Bow-tie filter 118 and a collimator 119, at the positions where X-rays generated by the x-ray generator 111 pass through. The collimator 119 is connected to a collimator controller 120. The scanner controller 115 is connected to the drive unit 116 and the collimator controller 120, and controls rotation and stop of the disc 114, and the aperture of the collimator 120.

The radiation detection device 121 may have any of the configurations of the first to the fourth embodiments, where the detector element substrates 20101 and the circuit substrates (e.g., 50101) are laminated.

The bed 102 incorporates a bed driver for moving the bed 102 with respect to the disc 114. The bed driver is connected to a bed controller 124 for controlling the amount of driving, and a bed movement-measuring unit 125.

The operation unit 106 incorporates an input-output unit 107 and an arithmetic unit 104. The input-output unit 107 is provided with a display controller 105, an input unit 103, and a storage unit 108. The display controller 105 is connected to a display unit 109.

The display controller 105 displays on the display unit 109, a display screen 1601 as described in the sixth embodiment, for instance. Furthermore, on the display screen, an operation screen is also displayed, allowing an operator to enter parameters via the input unit 103. The input unit 103 comprises a mouse and a keyboard, and the like, and accepts from the operator, inputting of parameters used for measurement and reconstruction, such as bed moving speed information and a reconstructing position.

The arithmetic unit 104 is provided with a correction processor 131, a reconstruction arithmetic unit 132, and an image processor 133.

The reconstruction arithmetic unit 132 comprises a reconstruction unit 132a for a current measurement image, and a reconstruction unit 132b for a photon measurement image. Output signals 312 from the A/D converter 310 as shown in FIG. 3(a) of the radiation detection device 121 are inputted in the reconstruction unit 132a for the current measurement image. Output signals 311 from the digital multiplexer 308 as shown in FIG. 3(a) are inputted in the reconstruction unit 132b for the photon measurement image.

Operations of each unit will be described. When the operator enters from the input unit 103, imaging conditions (such as the bed moving speed, tube current, tube voltage, and slice positions), and reconstruction parameters (such as an area of interest, a reconstructed image size, an inversely projected phase width, and a reconstruction filter function), according to such entries, the central control unit 126 outputs control signals necessary for imaging, to the x-ray controller 113, the bed controller 124, and the scanner controller 115. Then, when the operator manipulates the input unit 103 and outputs an imaging start signal, imaging starts.

When the imaging starts, the x-ray controller 113 transfers control signals to the high-voltage generator, high voltage is applied to the x-ray generator, and the subject 117 is irradiated with X-rays from the x-ray generator. Simultaneously, the scanner controller 115 transfers control signals to the drive unit 116, and then the disc 114 is rotated. Then, the x-ray generator 111 and the radiation detection device 121 go around the subject.

On the other hand, according to the control by the bed controller 124, the bed 102 placing the subject thereon moves in parallel to the body axis direction, or stops.

The X-rays emitted from the x-ray generator 111 are subjected to shaping of X-ray beams though the Bow-tie filter 118, then the collimator 119 restricts the irradiated region, and then the subject 117 is irradiated with thus obtained radiation. The X-rays are absorbed by (attenuate through) each tissue within the subject 117, pass through the subject 117, and are entered in the radiation detection device 121 at sampling intervals that are determined with respect to a direction of rotation. The unit of data collection in the direction of rotation is referred to as "view". The detector element substrate 20101 of the radiation detection device 121 has a configuration that the detector elements (D) are arranged two-dimensionally. The alignment of elements in the rotational direction is referred to as "channel", and the direction orthogonal thereto is referred to as "column".

According to the x-ray photons entered into the detector elements (D) on the detector element substrate 20101 of the radiation detection device 121, current pulse signals are generated, and the photon measurement data and the current measurement data are generated by the circuits on the circuit substrate 50101, as described in the first to the fourth embodiments. Then, the photon measurement data and the current measurement data are inputted into the reconstruction unit 132b for photon measurement image, and into the reconstruction unit 132a for current measurement image, in the form of output signals 311 and 312, respectively. The reconstruction unit 132b reconstructs a photon measurement image from the photon measurement data. The reconstruction unit 132a reconstructs a current measurement image from the current measurement data.

The reconstructed images are displayed on the display unit 105, as described in the sixth embodiment. The reconstructed images are stored in the storage unit 108.

The correction processor 131 performs following processes on the output signals 311 and 312 from the radiation detection device 121, such as an offset correction process, an air correction process, a reference correction process, a logarithmic transformation, and a phantom correction process for reducing beam-hardening effects. When the correction is performed, the reconstruction arithmetic unit 132 conducts the reconstruction process, with the use of thus corrected signals.

DESCRIPTION OF SYMBOLS 41, 43 bump, 42 Through Silicon Via (TSV), 0101a detector element (D), 121 radiation detection device, 301a photon measuring circuit (P), 302a integrator+adder (ASUM), 303a count adder (DSUM), 304a sample-hold circuit (S/H), 308 digital multiplexer (DMUX), 309 analogue multiplexer (AMUX), 310 A/D converter, 313a charge amplifier circuit, 20101 detector element substrate, 50101 circuit substrate

What is claimed is:

1. A radiation detection device comprising,
a plurality of detector elements for generating current pulse signals upon receipt of photons of radiation, and a photon measuring unit and a current measuring unit being connected to the detector elements, wherein,
the detector elements are arranged in a specified array, and every predetermined number of detector elements constitutes one detector pixel,
the photon measuring unit comprises a plurality of photon measuring circuits connected to the detector elements on a one-to-one basis, for counting the current pulse signals outputted from the detector elements,
the current measuring unit comprises an integrator, an adder, and a sample-hold circuit provided for every detector pixel, and a converter for converting an analogue signal to a digital signal, where one converter is provided for a plurality of the detector pixels, the integrator and the adder perform integration and addition of the current pulse signals outputted respectively from the plurality of detector elements constituting one detector pixel, the sample-hold circuit holds outputs of the addition and integration from the integrator and the adder, with a predetermined timing, and the converter selectively converts analogue outputs from the sample-hold circuit into digital signals, as to any of the plurality of detector pixels.

2. The radiation detection device according to claim 1, wherein,
the plurality of detector elements are mounted on a detector element substrate in the specified array, and the photon measuring unit and the current measuring unit are mounted on a circuit substrate, the detector element substrate and the circuit substrate being superimposed one on another, and a total circuit area of the photon measuring unit and the current measuring unit is equivalent to less than the area of the plurality of detector elements.

3. The radiation detection device according to claim 1, wherein,
the photon measuring unit further comprises a count adder provided for every detector pixel, and the count adder adds count results outputted from the plurality of photon measuring circuits respectively connected to the detector elements in one of the detector pixels.

4. The radiation detection device according to claim 3, wherein,
the photon measuring unit further comprises an output selector, one provided for the plurality of detector pixels, and the output selector selectively outputs from the count adders respectively provided for the plurality of the detector pixels.

5. The radiation detection device according to claim 1, wherein,
a length of wiring connecting the detector elements and the photon measuring circuits is shorter than the length of wiring from the detector elements up to the sample-hold circuit via the integrator and the adder.

6. The radiation detection device according to claim 5, wherein,
an operation time constant of the photon measuring circuit is shorter than the operation time constant of the sample-hold circuit.

7. The radiation detection device according to claim 1, wherein,
a wiring for outputting the current pulse signals from the detector elements branches into two, and one is connected to the photon measuring circuit, and the other is connected to the integrator.

8. The radiation detection device according to claim 1, wherein,
the integrator of the current measuring unit receives inputs not only of the current pulse signals outputted from the detector elements of the detector pixel being associated therewith, but also of the current pulse signals outputted from the detector elements of a second detector pixel being adjacent, and adds the current pulse signals from the two detector pixels.

9. The radiation detection device according to claim 8, wherein,
the current measuring unit further comprises a switch configured to select whether the current pulse signals outputted from the detector elements of the detector pixel are inputted into the integrator of the current measuring unit associated with the detector pixel, or into the integrator of the current measuring unit associated with the second detector pixel adjacent to the detector pixel.

10. The radiation detection device according to claim 8, further comprising,
a controller configured to stop the integrator, the adder, and the sample-hold circuit into which the current pulse signals are not inputted from the detector elements of the detector pixel being associated, when the current pulse signals outputted from the detector elements of the detector pixel being associated are inputted in the integrator of the second detector pixel being adjacent.

11. The radiation detection device according to claim 1, wherein,
the plurality of photon measuring circuits include a photon measuring circuit that receives inputs of current pulse signals outputted from a first detector element being associated therewith, as well as receiving inputs of current pulse signals outputted from a second detector element within the same detector pixel, and counts both the current pulse signals of the two detector elements.

12. The radiation detection device according to claim 11, wherein,
the photon measuring unit comprises a switch configured to select whether the current pulse signals outputted from the first detector element are inputted in the photon measuring circuit associated therewith, or the current pulse signals are inputted in the photon measuring circuit associated with the second detector element different from the first detector element.

13. The radiation detection device according to claim 11, further comprising,
a controller configured to stop the photon measuring circuit to which the current pulse signals are not inputted from the first detector element being associated, when the current pulse signals outputted from the first detector element being associated are inputted in the photon measuring circuit associated with the second detector element.

14. The radiation detection device according to claim 2, wherein,
the circuit substrate has divided regions; a region where the plurality of photon measuring circuits are provided, and a region where the integrator, the adder, the sample-hold circuit, and the converter are provided, and in the region for placing the photon measuring circuits, the photon measuring circuits are provided in an array.

15. The radiation detection device according to claim 14, wherein,
the region where the integrator, the adder, the sample-hold circuit, and the converter are provided comprises two band-like regions being orthogonal to each other in the longitudinal direction, and the integrator, the adder, and the sample-hold circuit are placed in one of the band-like regions, whereas the converter is placed in the other band-like region.

16. The radiation detection device according to claim 15, wherein,
the two band-like regions are placed in the center of the circuit substrate, and the region for placing the photon measuring circuits are divided into four regions, according to the two band-like regions.

17. The radiation detection device according to claim 15, wherein,
the two band-like regions are placed along two orthogonal sides of the circuit substrate.

18. The radiation detection device according to claim 2, wherein,
the circuit substrate comprises two substrates being laminated, and
among the photon measuring circuits, the integrator, the adder, the sample-hold circuit, and the converter, the photon measuring circuits are mounted on the substrate closer to the detector element substrate, out of the two substrates.

19. A medical imaging system comprising,
a radiation generator configured to output radiation, a radiation detection device configured to detect radiation that passes through a subject, and a reconstruction unit configured to reconstruct an image by using data detected by the radiation detection device, wherein,
the radiation detection device according to claim 1 is provided as the radiation detection device, and
the reconstruction unit incorporates a first reconstruction unit configured to generate a photon measurement image by using a measurement result of the photon measuring unit, and a second reconstruction unit configured to generate a current measurement image by using a measurement result of the current measuring unit.

20. The medical imaging system according to claim 19, further comprising,
a display controller configured to display on a display unit, both the photon measurement image and the current measurement image simultaneously.

* * * * *